US008132457B2

(12) United States Patent
Haji-Sheikh et al.

(10) Patent No.: US 8,132,457 B2
(45) Date of Patent: Mar. 13, 2012

(54) NANO-POROUS ALUMINA SENSOR

(75) Inventors: Michael Haji-Sheikh, DeKalb, IL (US); Anima Bose, DeKalb, IL (US); Leonard Wardzala, DeKalb, IL (US)

(73) Assignee: Northern Illinois University, DeKalb, IL (US)

( * ) Notice: Subject to any disclaimer, the term of this patent is extended or adjusted under 35 U.S.C. 154(b) by 642 days.

(21) Appl. No.: 12/228,225

(22) Filed: Aug. 11, 2008

(65) Prior Publication Data

US 2010/0031745 A1 Feb. 11, 2010

Related U.S. Application Data

(60) Provisional application No. 60/954,855, filed on Aug. 9, 2007.

(51) Int. Cl.
*G01N 19/00* (2006.01)
(52) U.S. Cl. .................................... 73/335.04
(58) Field of Classification Search ............... 73/335.04
See application file for complete search history.

(56) References Cited

U.S. PATENT DOCUMENTS

| | | | | |
|---|---|---|---|---|
| 4,276,128 | A * | 6/1981 | Nishino et al. | 205/200 |
| 4,768,012 | A * | 8/1988 | Williams et al. | 338/34 |
| 6,705,152 | B2 * | 3/2004 | Routkevitch et al. | 73/31.05 |
| 6,946,197 | B2 * | 9/2005 | Yadav et al. | 428/402 |
| 7,017,389 | B2 * | 3/2006 | Gouma | 73/31.05 |
| 2002/0118027 | A1 * | 8/2002 | Routkevitch et al. | 324/694 |
| 2007/0256941 | A1 * | 11/2007 | Prasad et al. | 205/775.5 |

OTHER PUBLICATIONS

Electrocatalytic reduction of platinum phosphate blue on carbon surfaces: A novel method for preparing fuel cell electrodes; Anima B. Bose, Mohosin Sarkar, Rathindra N. Bose; Journal of Power Sources 157, (2006), pp. 188-192.
Electrocatalytic reduction of platinum phosphate blue on carbon surfaces: A novel method for preparing fuel cell electrodes, Amina B. Bose, et al., Journal of Power Sources, vol. 157, pp. 188-192, 2006.
Electrical Impedance Response of a Thick-Thin film Hybrid Anodic Nanoporous Alumina Sensor to Methanol Vapors, Christopher Radzik, et al., International Journal on Smart Sensing and Intelligent Systems, vol. 1, No. 2, pp. 470-479, Jun. 2008.
Detection of cyclic volatile organic compounds using single-step anodized nanoporous alumina sensors, IEEE Sensors Journal, 2008.

* cited by examiner

*Primary Examiner* — Hezron E Williams
*Assistant Examiner* — Rodney T Frank
(74) *Attorney, Agent, or Firm* — Kohn & Associates PLLC

(57) ABSTRACT

A nano-sensor including a substrate including pores formed thereon and a detecting mechanism for detecting changes in capacitance due to the presence of a substance. A method of measuring humidity by sampling air with the nano-sensor, detecting changes in capacitance, and determining the relative humidity of air. A method of detecting the presence of a substance by taking a sample with the nano-sensor, detecting changes in capacitance, and determining the presence of a substance. A method of making the nano-sensor by forming nano-pores on a substrate, and forming, on the surface of the substrate, a detecting mechanism for detecting changes in capacitance due to the presence of a substance.

16 Claims, 24 Drawing Sheets

NANO-POROUS ALUMINA SENSOR

CROSS-REFERENCE TO RELATED APPLICATIONS

This application claims the benefit of priority under 35 U.S.C. Section 119(e) of U.S. Provisional Patent Application No. 60/954,855, filed Aug. 9, 2007, which is incorporated herein by reference.

BACKGROUND OF THE INVENTION

1. Field of the Invention

Generally, the present invention relates to a nano-sensor. More specifically, the present invention relates to a sensor for use in detecting humidity.

2. Description of Related Art

Humidity sensors are utilized in a variety of sensing applications and can be implemented in the context of semiconductor-based sensors utilized in many industrial applications. Solid-state semiconductor devices are found in most electronic components today. Semiconductor-based sensors are generally fabricated using semiconductor processes.

Many modern processes require measurement of relative humidity at dew points between −40 C and 180 C, corresponding to relative humidity between 1% and 100%. There is a need for a durable, compact, efficient moisture detector that can be used effectively in these processes to measure very small moisture content in gaseous atmospheres.

Humidity can be measured by a number of techniques. In a semiconductor-based system, humidity can be measured based upon the reversible water absorption characteristics of polymeric materials. The absorption of water into a sensor structure causes a number of physical changes in the active polymer. These physical changes can be sensed by electrical signals which are related to the water concentration in the polymer and which, in turn, are related to the relative humidity in the air surrounding the polymer.

Two of the most common physical changes are the change in resistance and the change in dielectric constant, which can be respectively translated into a resistance change or a capacitance change. It has been found, however, that elements utilized as resistive components suffer from an inherent dissipation effect caused by the dissipation of heat due to the current flow in the elements necessary to make a resistance measurement. This disadvantage results in inaccurate or erroneous readings, among other problems.

Elements constructed to approximate a pure capacitance avoid the disadvantages of the resistive elements. It is important in the construction of capacitive elements, however, to avoid problems that can arise with certain constructions for such elements. In addition, there can also be inaccuracy at high relative humidity values. High water content causes problems due to excessive stress and resulting mechanical shifts in the components of the element. By making the component parts of the element thin, it has been found that the above-mentioned problems can be avoided and the capacitance type element can provide a fast, precise measurement of the relative humidity content over an extreme range of humidity as well as over an extreme range of temperature and pressure and other environmental variables. However, even thin polymer films suffer from stress-related problems.

Humidity-sensing elements of the capacitance-sensing type usually include a moisture-insensitive, non-conducting substrate structure with appropriate electrode elements mounted or deposited on the structure along with a layer or coating of dielectric, highly moisture-sensitive material overlaying the electrodes and positioned so as to be capable of absorbing water from the surrounding atmosphere and reaching equilibrium in a short period of time. Capacitive humidity sensors are typically constructed by depositing several layers of material on a substrate material. One example of a humidity sensor is disclosed in U.S. Pat. No. 6,724,612.

Conventional humidity sensors are continually plagued with inaccurate output due to disruption of the sensing polymer from condensation. A need exists for configuring and providing humidity sensor structures that overcome the above referenced problems.

SUMMARY OF THE INVENTION

The present invention provides a nano-sensor including a substrate having pores formed thereon and a detecting mechanism for detecting changes in capacitance due to the presence of a substance.

The present invention also provides for a method of measuring humidity, including the steps of sampling air with the nano-sensor, detecting changes in capacitance, and determining the relative humidity of air.

The present invention provides for a method of detecting the presence of a substance, including the steps of taking a sample with the nano-sensor, detecting changes in capacitance, and determining the presence of a substance.

The present invention further provides for a method of making the nano-sensor, including the steps of forming nanopores on a substrate, and forming, on the surface of the substrate, a detecting mechanism for detecting changes in capacitance due to the presence of a substance.

BRIEF DESCRIPTION OF THE DRAWINGS

Other advantages of the present invention will be readily appreciated as the same becomes better understood by reference of the following detailed description when considered in connection with the accompanying drawings wherein.

DETAILED DESCRIPTION OF THE INVENTION

Figure 1A:
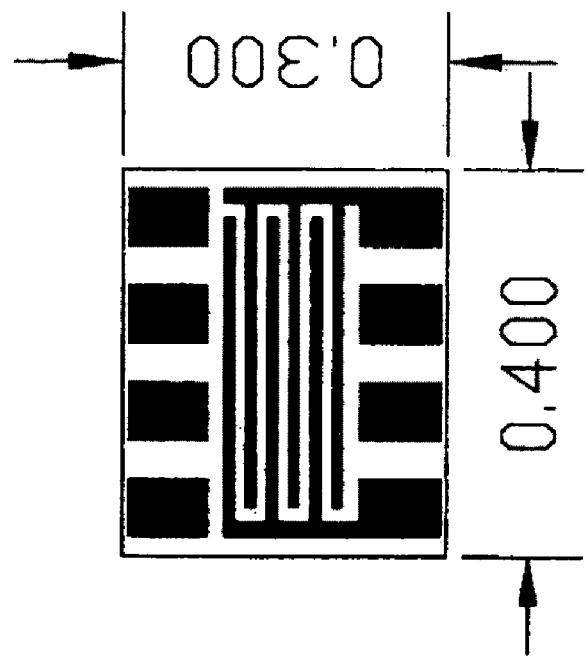
FIGS. 1A and 1B are mechanical views of the nano-sensor of the present invention.
Figure 1B:
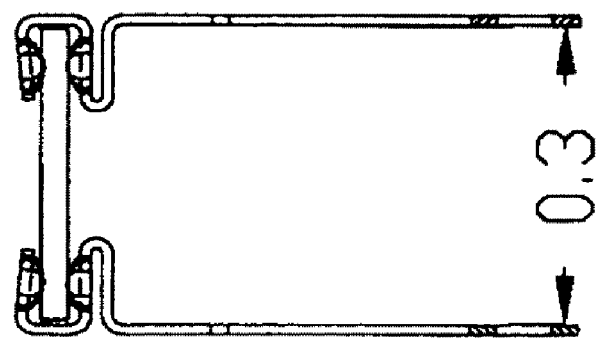
Figure 2:
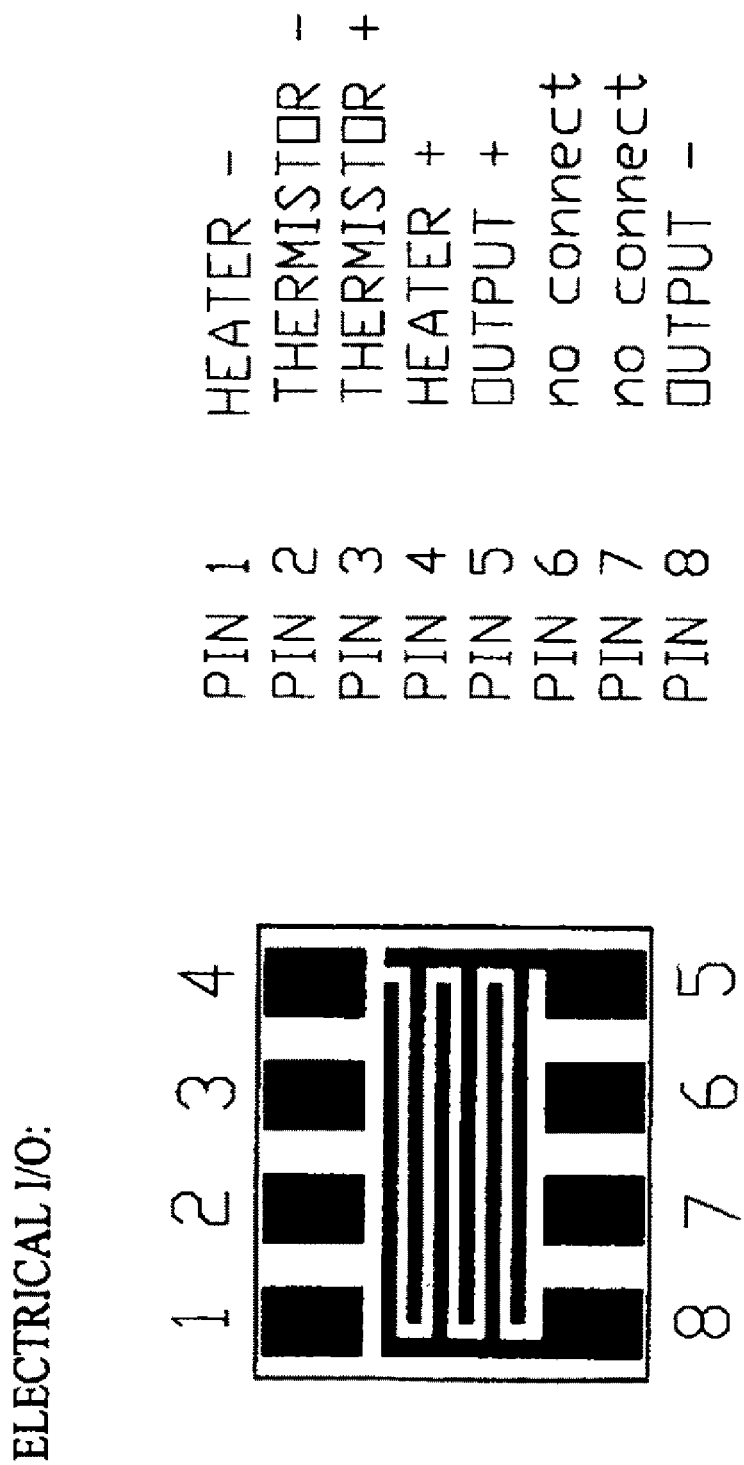
FIG. 2 is an electrical I/O view of the nano-sensor, wherein the identity of each pin is provided.
Figure 23:
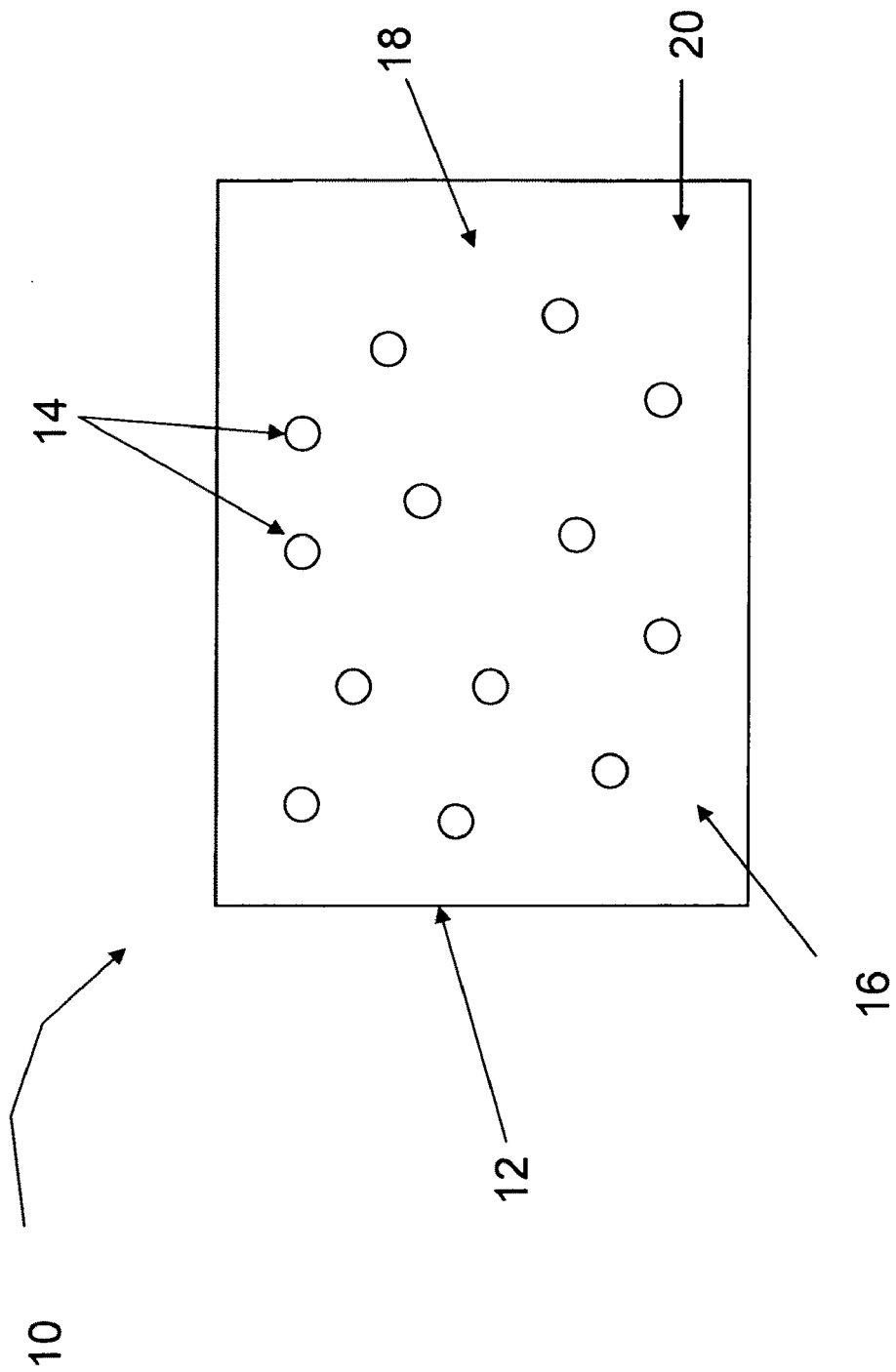
FIG. 23 is a top view of the nano-sensor.

The present invention is a nano-sensor, generally shown at 10 in FIG. 23, as well as mechanical depictions in FIGS. 1A, 1B, and 2. The nano-sensor 10 includes a substrate 12 having pores 14 formed thereon and a detecting mechanism 16 for detecting changes in capacitance due to the presence of a substance.

"Substance" as used herein, refers to any chemical compound in a solid, liquid, or gaseous form that is detectable by the nano-sensor of the present invention. For example, the substance can be water, and the nano-sensor can be used to detect humidity of the air. The substance can also be any other chemical compound, and several other examples are described herein.

The term "alumina" as used herein, is intended to include self-organized nano-porous anodic aluminum oxide, which is well known to those of skill in the art.

The substrate 12 of the nano-sensor 10 is preferably made of alumina and is non-conductive. More specifically, the nano-sensor 10 is formed of an alumina substrate onto which is deposited aluminum anodized into a film of nano-porous alumina oxide or anodic nano-porous oxide. Alternatively, the nano-sensor 10 can be formed of any other ceramic substrate (or silicon), examples of which are known to those of skill in the art. The film is deposited using thick and thin film techniques as shown in the figures. The method of forming the film enable pores 14 to be formed on the film.

The detecting mechanism 16 includes a metal surface 18 operatively attached to the substrate, and a power source 20, wherein the power source 20 produces an electric current on the metal surface 18. Preferably, the metal surface 18 is platinum or aluminum. The power source 20 can be internal or external to the nano-sensor 10. The thin-film metal surface 18 is robust and does not corrode in moisture, acidity, or other chemical environments due to its inherent inert chemical reactivity. The thin-film metal surface 18 is, however, a highly conductive metallic surface that catalyzes oxidation and reduction reactions upon application of an electric potential. The output electrical signal, as either current or capacitance, is proportional to the concentration of the oxidizing or reducing agents, and therefore the magnitudes of the signals can be quantitatively equated with the amount of analytes (i.e., substances to be detected).

The nano-sensor 10 detects substances by the creation of a disturbance in the capacitance of the nano-sensor 10 by the substance to be sensed. An electric current is applied across the nano-sensor 10 by either the internal or external power source 20, and thus any disturbances in the capacitance across the nano-sensor 10 are detected. In other words, the nano-sensor 10 functions by detecting changes in capacitance. The use of the nano-sensor 10 in various applications is further described below.

The nano-sensor 10 of the present invention can be used in many different applications, such as, but not limited to, heating and refrigeration industries, food industries, medical industries, and fuel cell industries. The nano-sensor 10 can be used in instrumentation in environmental systems, fuel cell humidification systems, and planetary soil moisture measurements. The nano-sensor 10 can be used for hydrogen sensing for safety applications and fuel cell fuel mixtures. Specific designs for these uses are further described below.

The present invention provides for a method of measuring humidity, including the steps of sampling air with the nano-sensor, detecting changes in capacitance, and determining the relative humidity of air. More specifically, a disturbance is detected in capacitance of electric current applied across the nano-sensor 10 by the power source 20 due to the presence of water in the air. The relative humidity of air is determined by analyzing an output electrical signal that is proportional to a concentration of oxidizing or reducing agents on the metal surface 18 of the nano-sensor 10.

The present invention also provides for more generally a method of detecting the presence of a substance, including the steps of taking a sample with the nano-sensor, detecting changes in capacitance, and determining the presence of a substance. More specifically, a disturbance is detected in capacitance of electric current applied across the nano-sensor 10 by the power source 20 due to the presence of the substance. The presence of the substance is determined by analyzing an output electrical signal that is proportional to a concentration of oxidizing or reducing agents on the metal surface 20 of the nano-sensor 10.

For example, the nano-sensor 10 of the present invention can be used as a chemical sensor. The nano-sensor 10 can be unmodified, or modified with a chemical detecting compound condensed inside the pores 14 of the nano-sensor 10. For example, the chemical detecting molecule can be an organic molecule such as acetone. Also, a hydrophobic filter can be operatively attached to the substrate 12 (such as polytetrafluoroethylene (PTFE) film). In this case, the sample is taken by hydrophobically filtering molecules that are the substances to be detected. With the filter, the nano-sensor 10 can be used to sense organic compositions such as methanol, ethanol, propanol, isopropanol (IPA), butanol, acetone, cyclohexane, cyclohexene, benzene, toluene, o-xylene, m-xylene, p-xylene, ammonia, and also water.

Additionally, the nano-sensor 10 can be modified to include a mechanism that separates the signals from different substances electrically within a single nano-sensor 10. In other words, a single nano-sensor 10 can be used to sense multiple compounds or compositions, wherein the nano-sensor 10 can be designed to provide a different output or signal based upon the compound to be detected.

Also, the nano-sensor 10 of the present invention can be used for sensing gases. Using electroplating, the chemical detecting compound can be grown at the bottom of the pores 14 on the nano-sensor 10. By selecting different chemical detecting compounds, a nano-sensor 10 can be created that can discriminate between multiple gases. An example of such selectivity includes, but is not limited to, the use of palladium to sense $H_2$. Palladium whiskers can absorb $H_2$ and turn into palladium hydride. Palladium hydride has a different permiativity then pure palladium and thus enables the nano-sensor 10 to sense the presence of $H_2$. The nano-sensor 10 thus functions as a "chemical nose" capable of detecting the presence of gases or other compositions.

Figure 5:
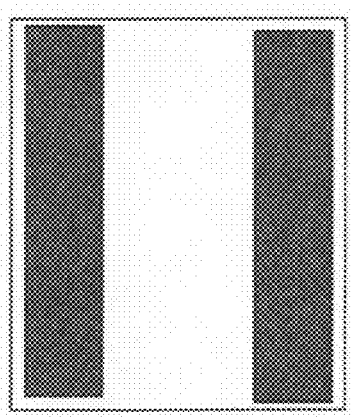
FIG. 5 is a representation of the thick film deposition front of the nano-sensor of the dielectric for the I/O pad.
Figure 4:
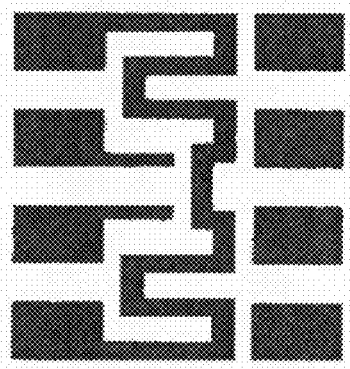
FIG. 4 is a representation of the thick film deposition back of the nano-sensor of the conductor, I/O pads, heater, and thermistor terminations.
Figure 3:
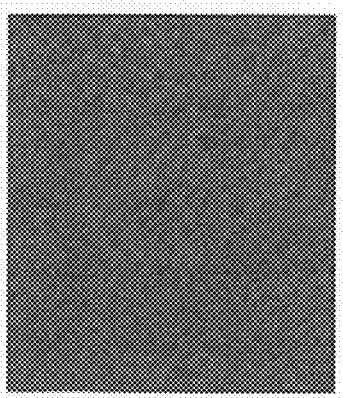
FIG. 3 is a representation of the thick film deposition front of the nano-sensor on alumina-smoothing glass.

The nano-sensor 10 is preferably made as follows. A ceramic substrate is cleaned on both sides with deionized water. The front of the substrate is printed with a thick film smoothing glass layer using a screen printer, as shown in FIG. 3. This layer is dried at 150 C and then fired in a BTU furnace using a 900 C profile. The back of the substrate is printed with a thick film conductor using a screen printer to create a heater and I/O pads for a thermistor, as shown in FIG. 4. This layer is dried at 150 C and then fired in a BTU furnace using an 850 C profile. The back is then printed with a thick film thermistor material using a screen printer. This layer is dried at 150 C and then fired in a BTU furnace using an 850 C profile. Next, TiW is evaporated onto the front. Then aluminum is evaporated onto the front. These thin film layers are then anodized to create a nano-porous ceramic layer. An insulating layer is then printed on the top surface using a thick film dielectric material, as shown in FIG. 5. This insulating layer is only printed in the area under the I/O pads to create a buffer layer. This layer is dried at 150 C and then fired in a BTU furnace using a 600 C profile. Finally, an interdigitated finger pattern is printed over the nano-porous area with the I/O pads printed over the buffer layer. This layer is printed with a thick film conductor material that is dried at 150 C and then fired in a BTU furnace using a 500 C profile. One skilled in the art is also familiar with other standard methods of production and these can also be used.

This technique can also be integrated into a semiconductor circuit. The nano-porous material can be put directly on a gate of a MOS device then patterned and etched. This material can then be treated as described herein. The resulting nano-sensor has the advantages of being able to be used in broader temperature ranges, provides a faster response time, and provides a greater response signal.

Figure 6:
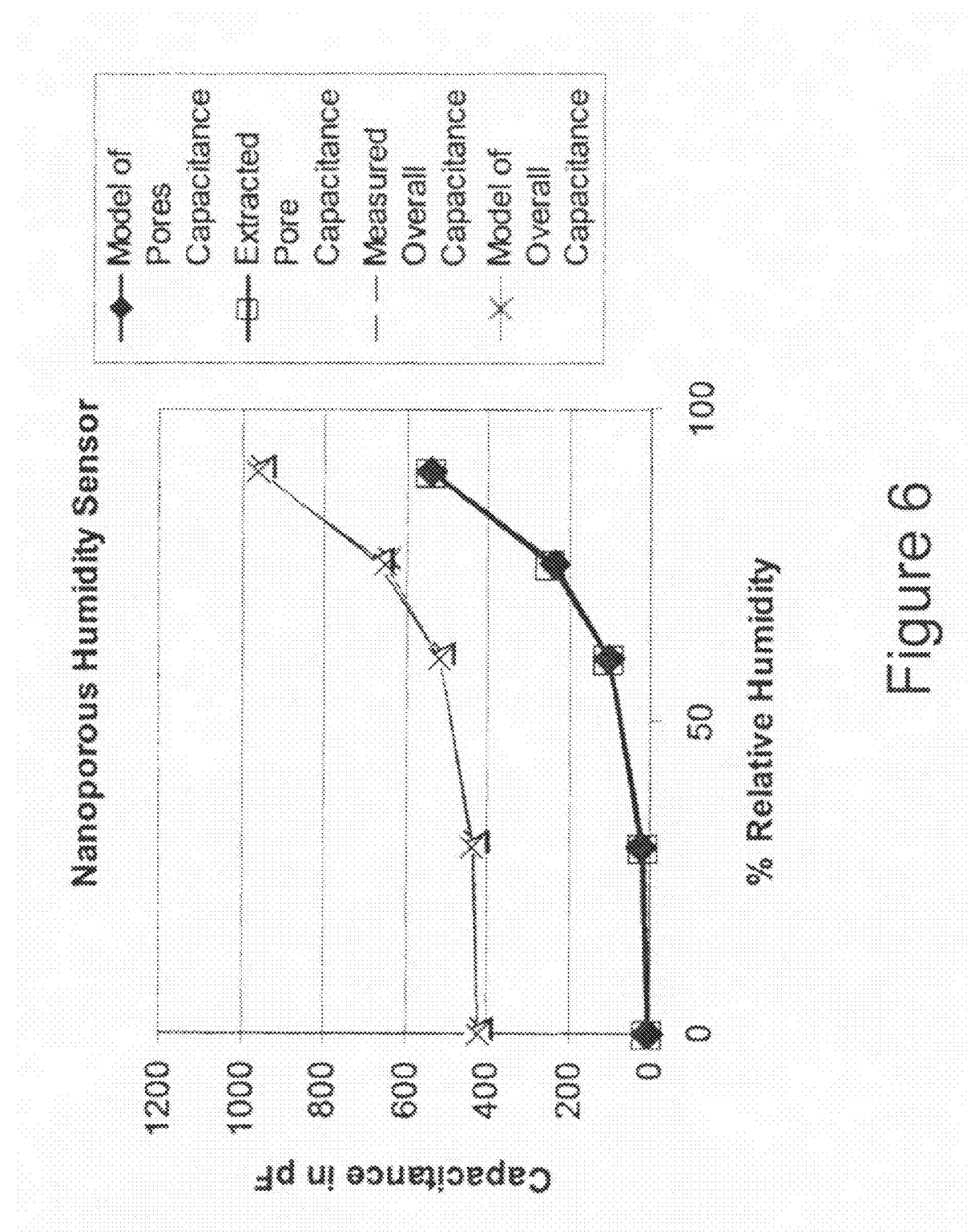
FIG. 6 is a graph of capacitance versus percent relative humidity as measured with the nano-sensor.

The nano-sensor 10 of the present invention was used to measure capacitance (in pF) as a function of percent relative humidity, as shown in FIG. 6. Both pore capacitance and overall capacitance were measured with the nano-sensor and compared to models of pore capacitance and overall capacitance. Both measurements provided an excellent fit to the model curves and confirm that the nano-sensor provides accurate measurements of relative humidity.

The detecting mechanism 16 is formed by a three-electrode setup that includes a substrate serving as the working electrode, a platinum foil functioning as an auxiliary, and a reference electrode being an Ag/AgCl electrode. The substrates are submerged in dilute solutions of tetrameric platinum phosphate blue complex containing an electrolyte. The electrolyte can be any electrolyte able to function in the manner disclosed herein. The platinum solution is preferably between 2 to 5 mM concentration in 0.1 M $NaClO_4$ for use in the coating purposes. Potentials are then applied by a potentiostat/galvanostat and cycled between +1.0 to −1.0 V against the reference electrode with scan rates from 5 mV/s to 100 mv/s.

The platinum complex is first polymerized on the surface of the substrate by scanning the potential to negative direction and then reducing as a thin-film of platinum metal. By cycling the potential to positive direction, loosely bound platinum atoms are oxidized back to the solution. Other platinum compounds including potassium tetrachloroplatinate can also be used instead of the phosphate blue.

The platinum thin-films are strongly anchored to the surfaces of the substrates due to the removal of any loosely bound platinum atoms at positive potentials due to reoxidation. Thin-film surfaces with variable thicknesses including a mono-layer of platinum were generated. The thickness can be controlled by the scan rates and number of cycles during the coating process. Higher film thickness can be prepared by lower scan rates and higher starting platinum concentrations. The average platinum cluster sizes can be controlled between 9 to 16 nm.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

EXAMPLES

Use of a Conductive Adhesion Layer to Produce a Nano-Porous Sensor

Experimental Procedure

To produce the thin-film nano-pores, the starting substrate material was alumina. This substrate material was chosen for its low cost and ease of use. A smoothing material was printed on the alumina to make the substrate compatible with thin film deposition. This smoothing layer process produces approximately 6000 nanometers (nm) of oxide. All processing was performed in a class-1000 clean room to minimize the effects of particles and impurities in the thick film material and the depositions took place in a Class 100 clean room. Initial experiments with thermally evaporated aluminum films on $SiO_2$ showed that an electrically conductive adhesion layer would be required to produce a robust anodically anodized oxide film on the substrate. This experiment showed that the film started to grow non-uniformly anodized nano-pores that made the film problematic for use.

Figure 7:
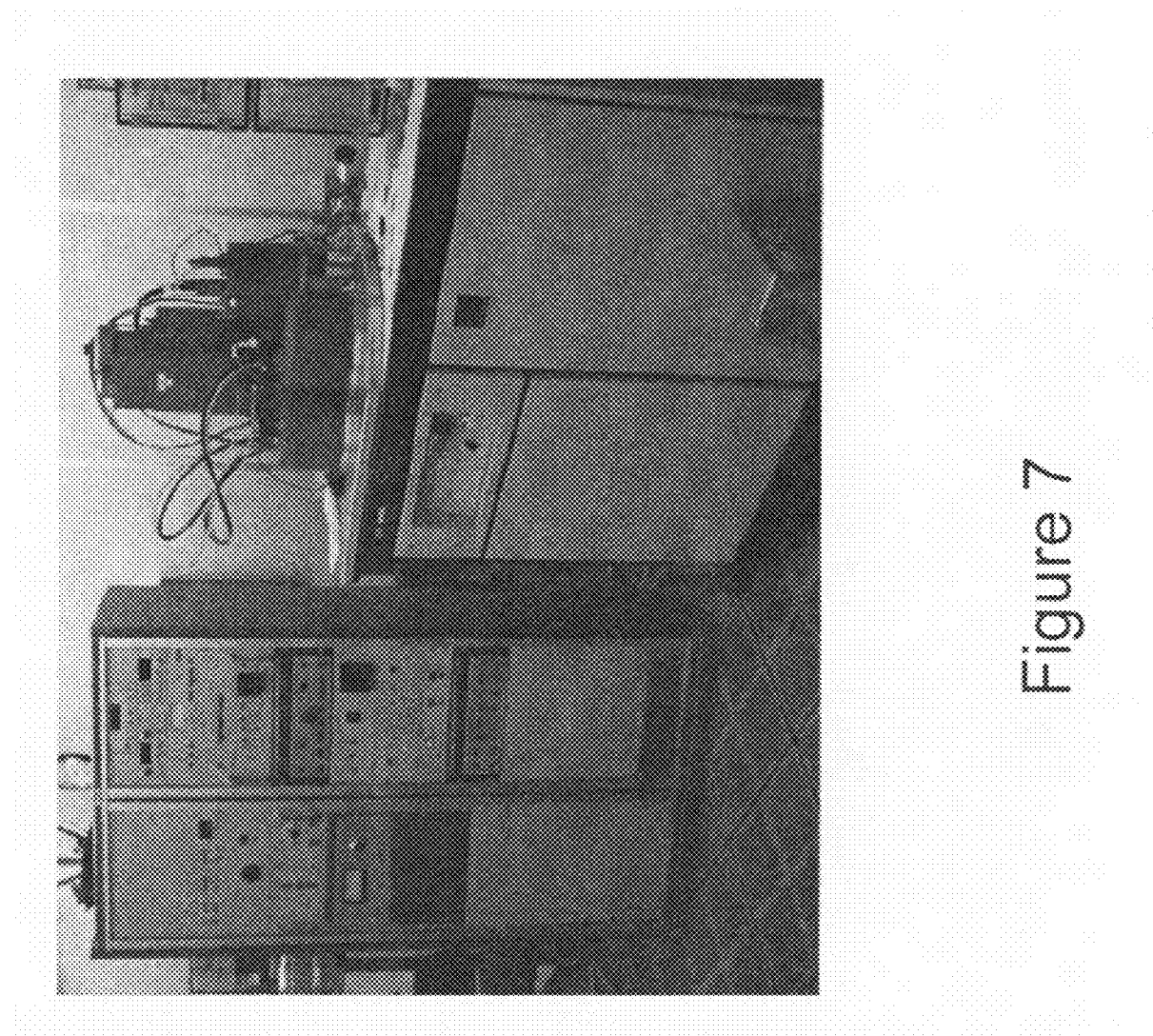
FIG. 7 is a photograph of a sputter deposition system.

The system chosen (shown in FIG. 7) to produce the adhesion layer and the aluminum film is a production capable CVC, Inc deposition system (heretofore called the CVC system) with two DC magnetron targets and one RF target. This sputter deposition system is capable of depositing on substrates, which are as large as 6 inches. This system is cryo-pumped with a base pressure measured at $1.1 \times 10^{-7}$ torr.

The "glue" or adhesion layer selected was TiW due to its high affinity to both the aluminum film and $SiO_2$. This TiW layer is also very conductive (also with nanoscale grains) and will anodize in oxalic acid. The TiW layer was exposed to 3% (wt/wt) oxalic acid at 40 V for several hours in the initial experiments. This is similar to the case presented by Mukherjee et. al. who anodized tungsten to form anodic nanoporous tungsten oxide in a tungsten film using oxalic acid. The film was then measured for resistivity with a 4-point probe and the resistance had changed little. This resistance measurement indicates that either the $WO_3$ is conductive or not very thick. The CVC was designed to deposit large wafer batches with a rotating anode. This rotation velocity can be varied. The rotation chosen allowed the substrates to be exposed to the plasma for three seconds at a time at 600 W and 2 mTorr. This allows the system to build a film with multiple sub-monolayer depositions. The time calculated to produce a film of one micron of aluminum is 120 minutes and the time to produce the 0.1 µm of TiW glue layer is 20 minutes. To verify the thickness, the wafers were patterned using photolithography. This patterning creates a step in the aluminum that can facilitate thickness measurements. These measurements were made with an atomic force microscope (AFM). The Atomic force microscope used throughout this experiment is a Quesant Q-Scope 350 running in broadband wave mode.

Figure 8:
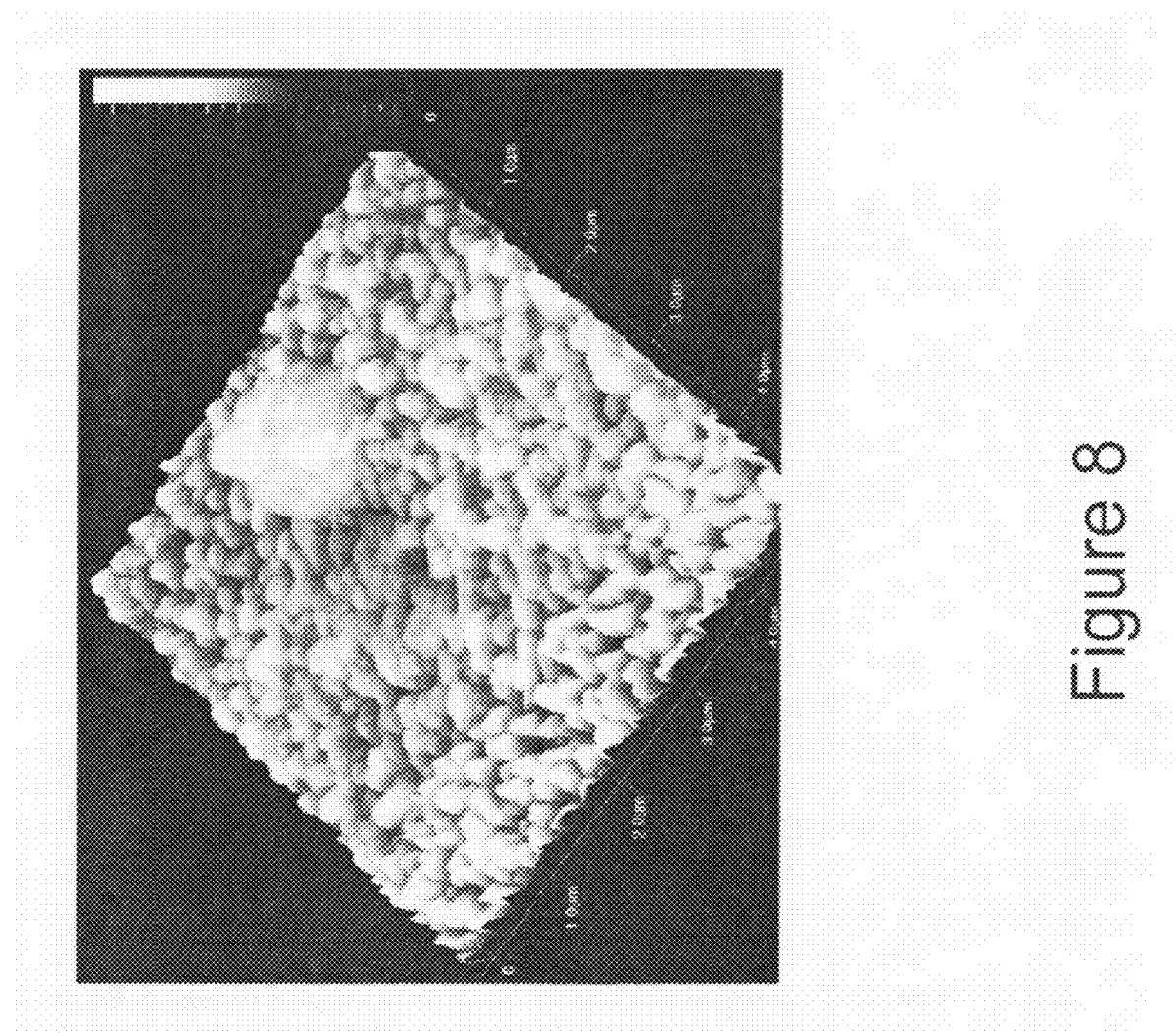
FIG. 8 is an AFM scan of the as-deposited nanofilm.

The AFM scan of the as-deposited film is shown in FIG. 8. The average grain size of this film is between 200 nm and 300 nm. This is important to note since the maximum number of pores that can fit in a single grain can be no more than 30 pores. This film does have a few large grains but these are not the majority. The large grains affect the reflectivity therefore creating a slight haze to the otherwise mirror like surface.

Figure 9:
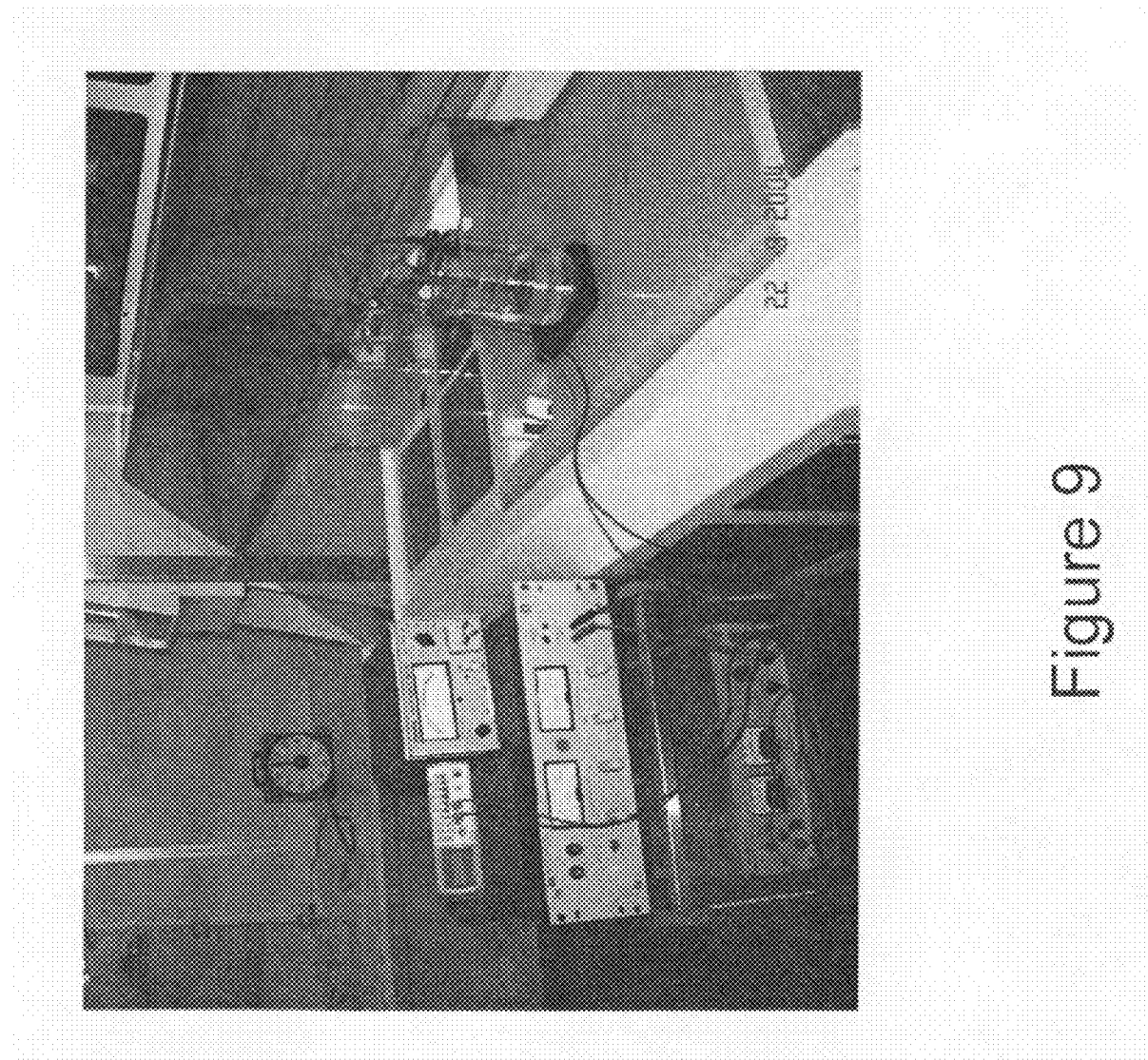
FIG. 9 is a simple electrochemical cell for anodizing thin films with a power supply that produces 45V at 6 A.
Figure 10:
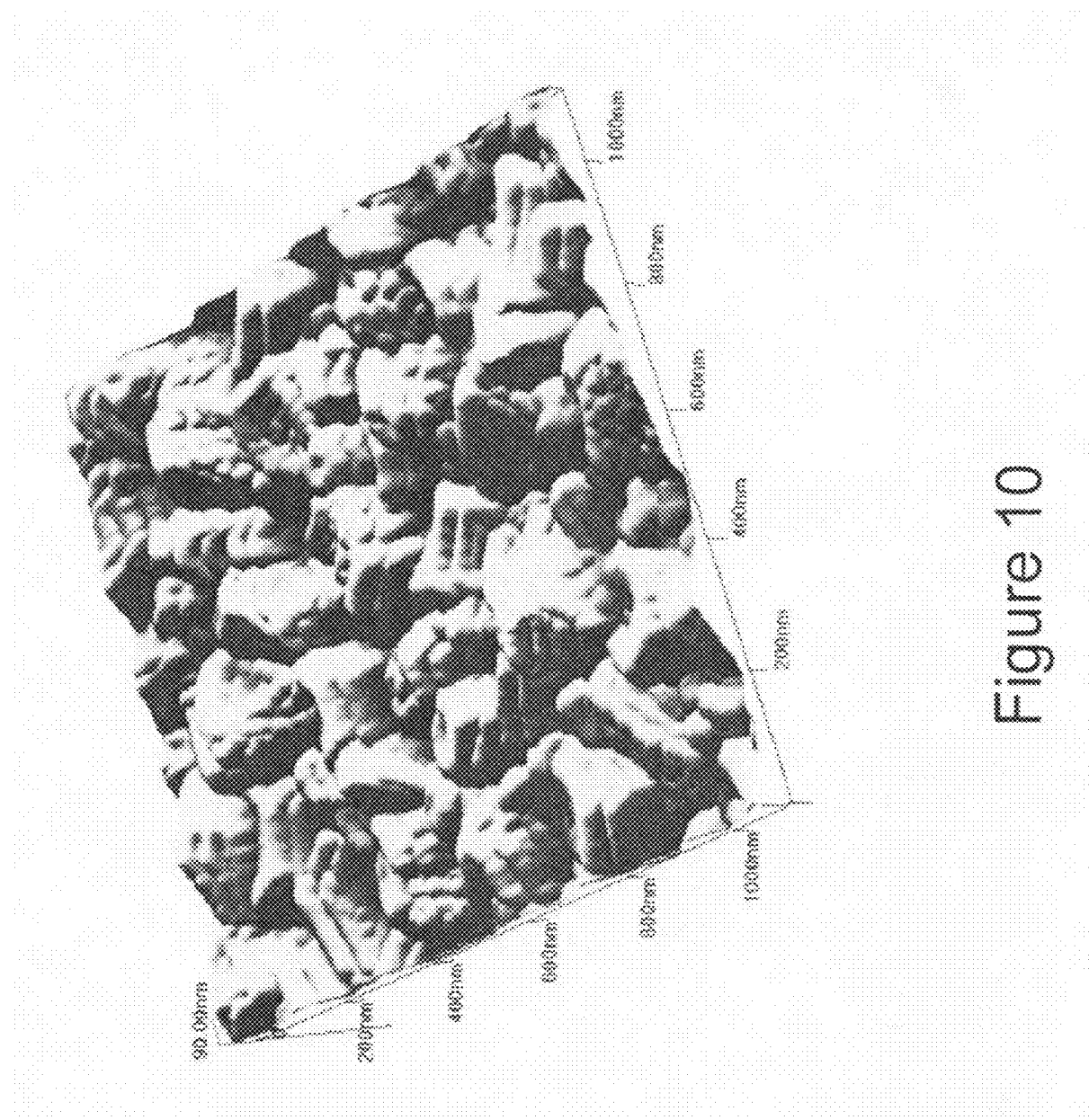
FIG. 10 is an atomic force microscopy of the anodic anodized oxide (AAO) film: the average nanopore is 40 nm in diameter and the original deposited aluminum grain size was 300 nm.

The film after anodization for thirty minutes at 25° C. and 40 volts in a simple electrochemical cell has a slightly blue to green appearance. Since the substrate was connected at a point with a clip lead, there is a slight color gradient. Additionally, the metal thickness created an additional color gradient. The anodization setup is shown in FIG. 9. The cathode in this setup is platinum while the anode is the silicon wafer coated in TiW/Al. The substrate was then rinsed for 15 minutes in deionized water then spin-rinsed and spin-dried. Using a four-point probe, this anodized film was determined to be non-conductive. To verify the porosity without using imaging, two clip leads were attached, one to the substrate and one to the film. The leads were then connected to a capacitance meter. The wafer was then exposed to water saturated air and if the wafer was properly anodized the capacitance would change by a factor of two. FIG. 10 shows an AFM scan of the anodic anodized oxide (AAO) film. Since the as-deposited film has a preferred orientation of (111), the pores are on the side of the "pyramidal" grains.

Thick-thin film hybrid AAO sensors were manufactured using alumina substrates. The surfaces of these substrates were specially prepared for the deposition of thin-film aluminum (1 micron) and the aluminum was then anodized in room temperature 4% oxalic acid. An interdigitated capacitor was then patterned on the surface of the AAO using a screen printed conductor and fired on a belt furnace. This thick-thin film sensor had leads soldered on in a dual pin configuration that allows for easy handling and measurement.

Results

Figure 11:
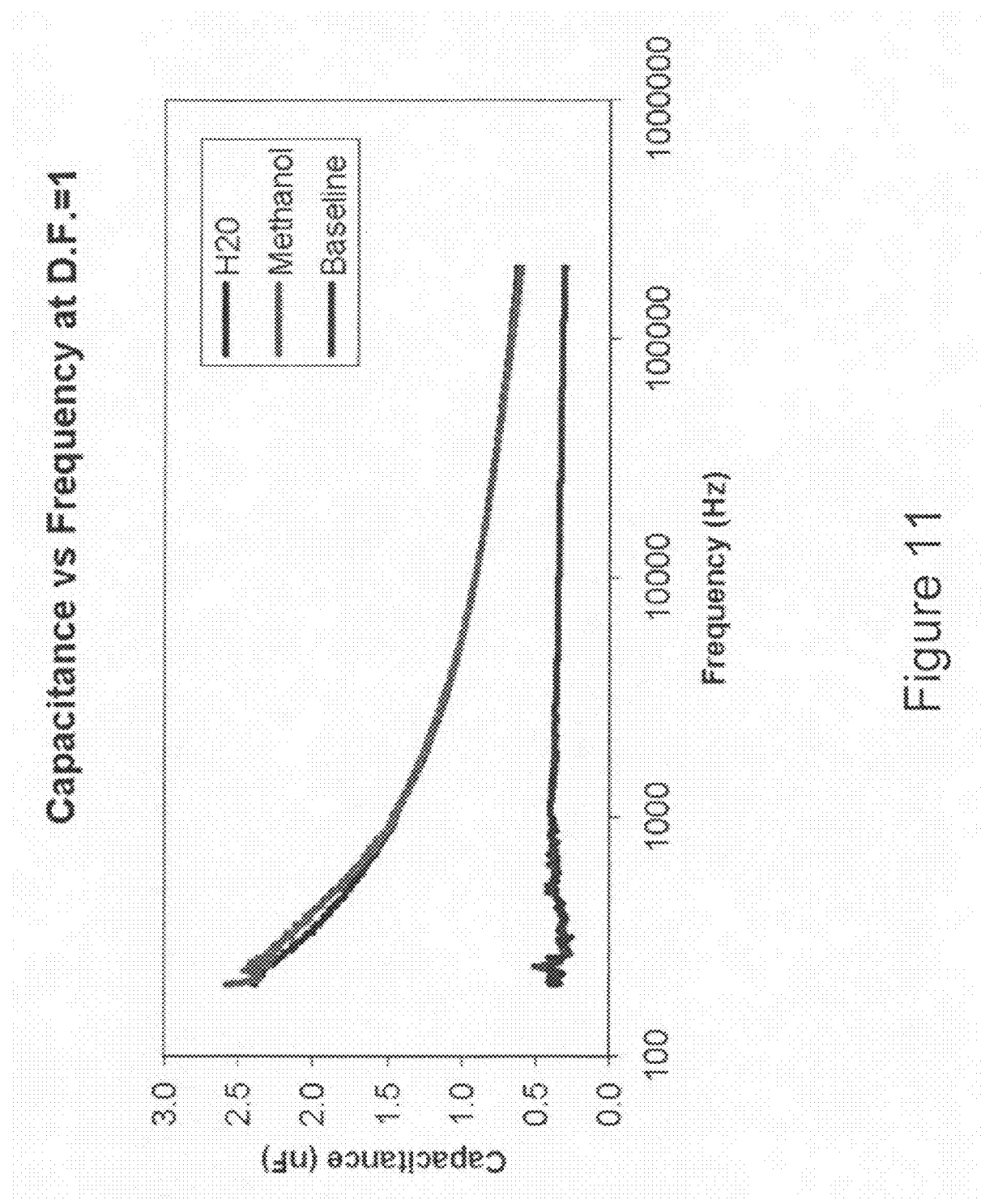
FIG. 11 is a graph of capacitance versus frequency for the AAO sensor when exposed to water and methanol.
Figure 12:
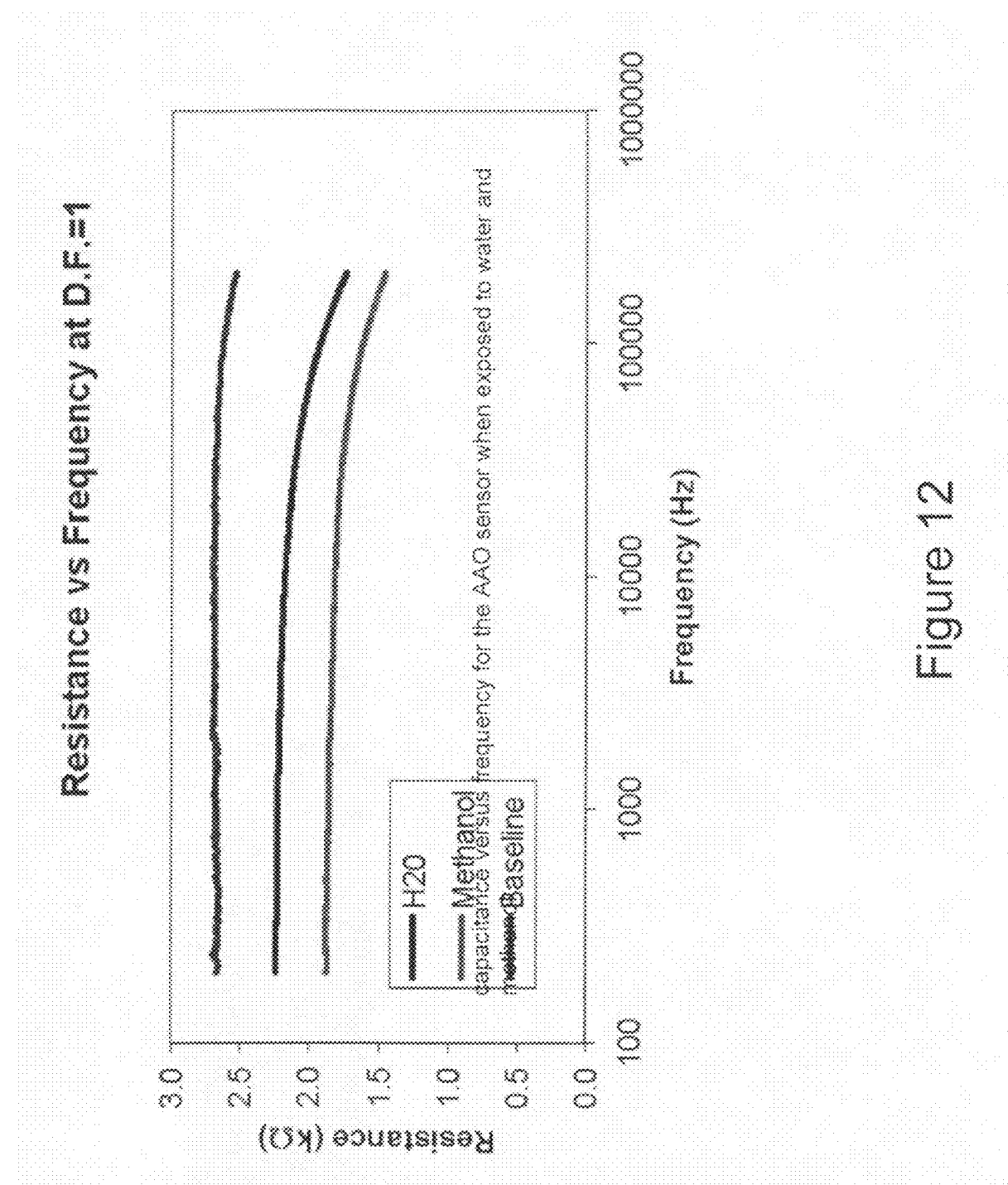
FIG. 12 is a graph of resistance versus frequency for the AAO sensor when exposed to water and methanol.
Figure 13:
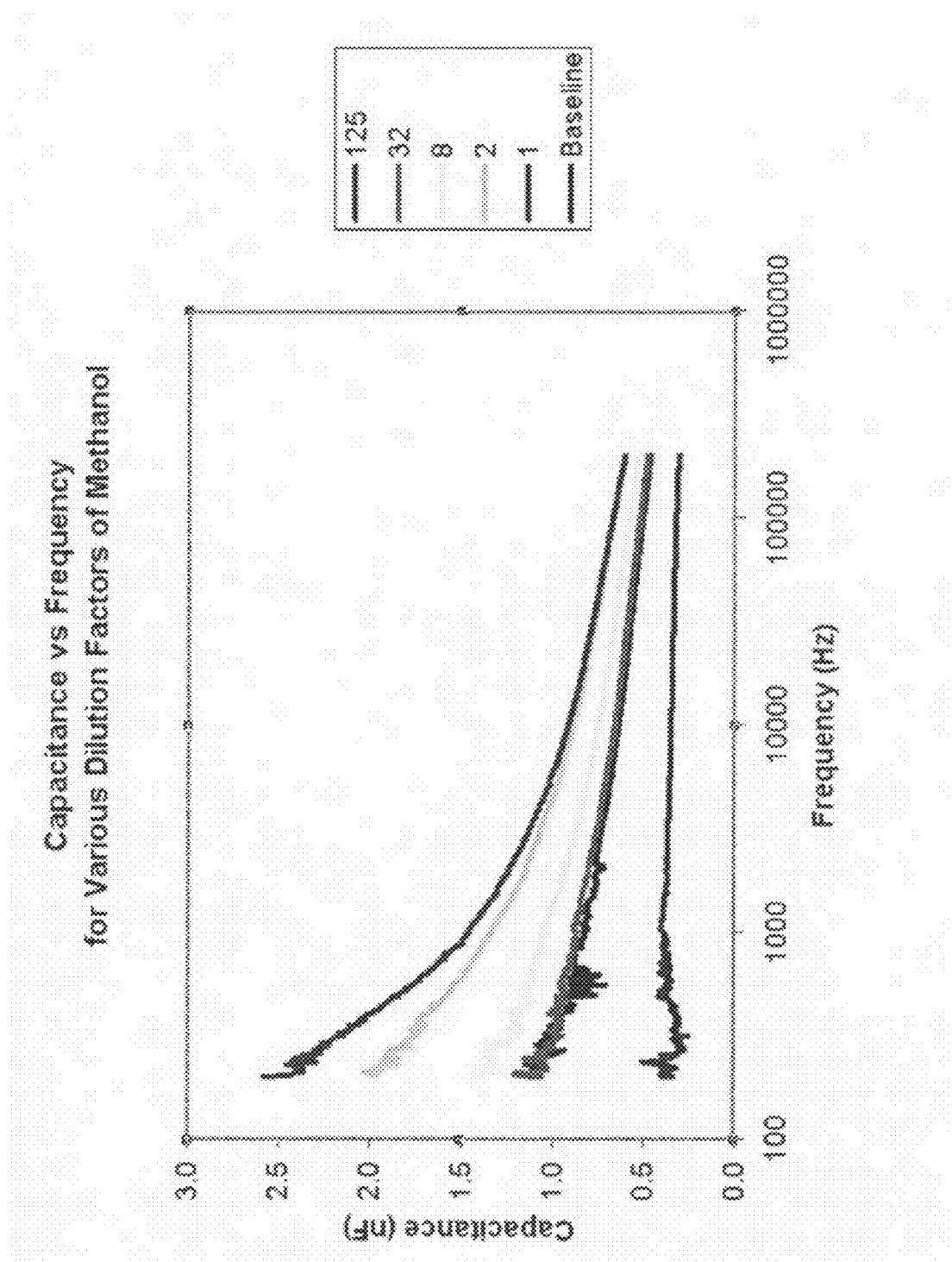
FIG. 13 is a graph of capacitance versus frequency for various dilution factors of methanol.
Figure 14:
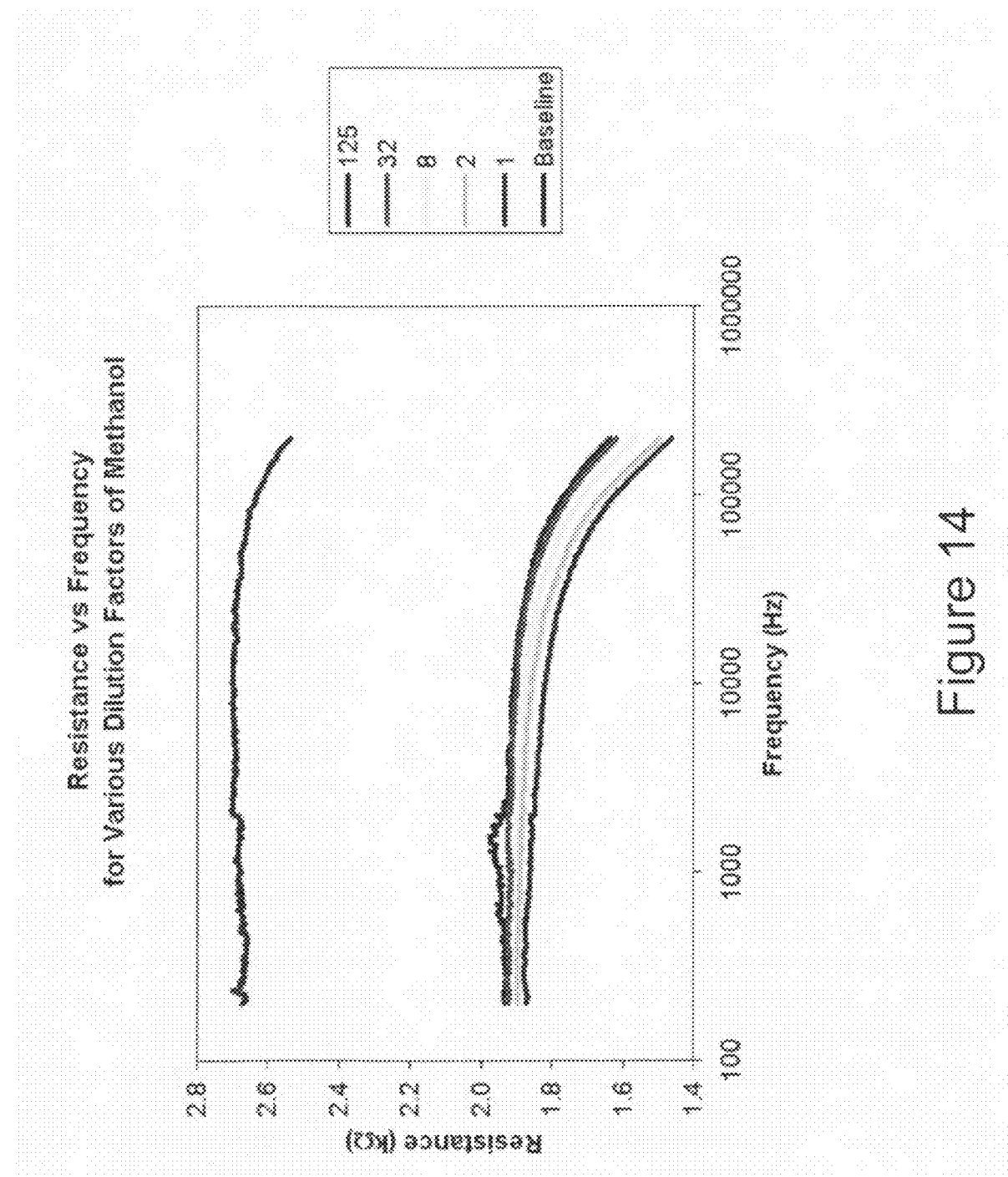
FIG. 14 is a graph of resistance versus frequency for various dilution factors of methanol.
Figure 15:
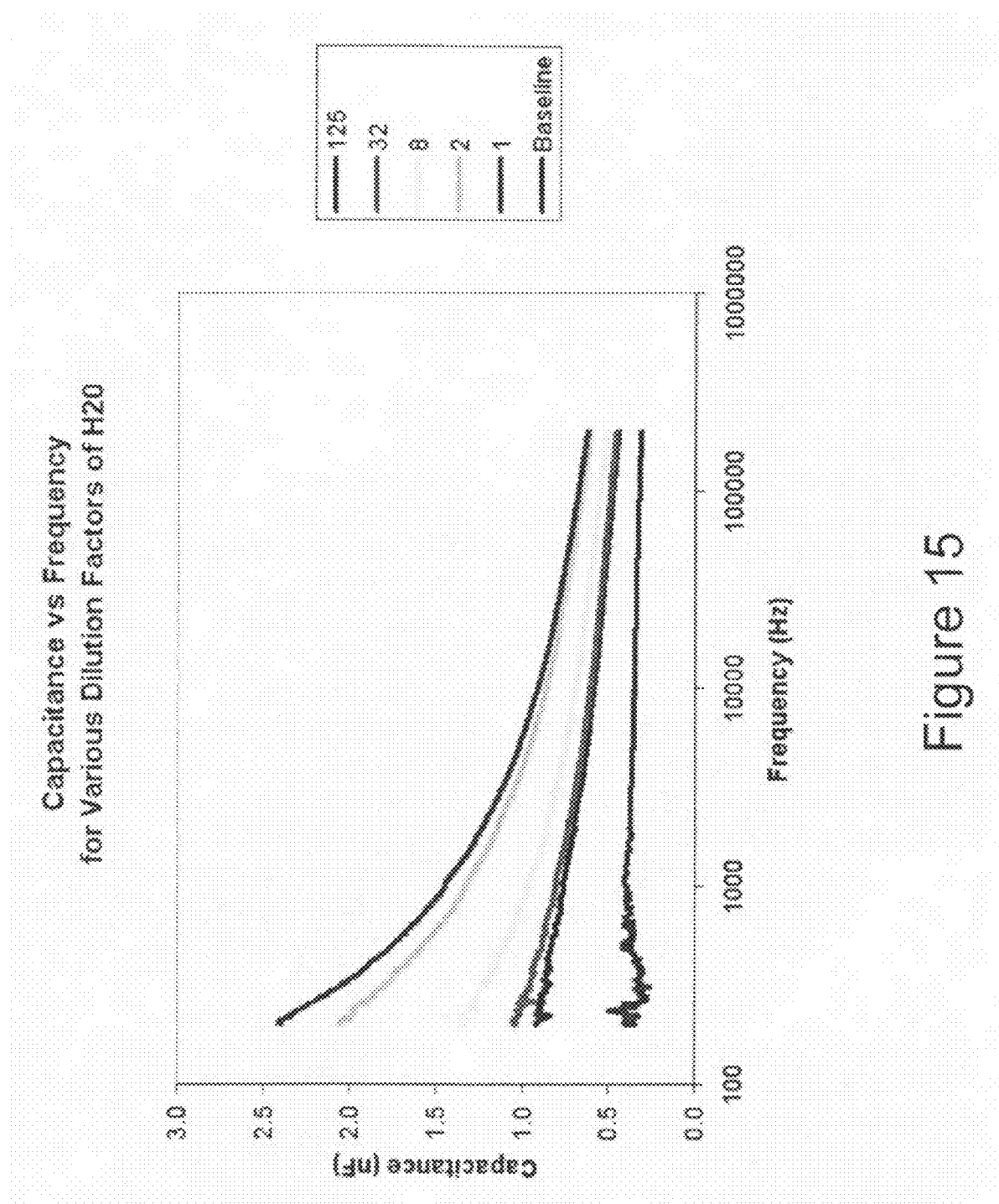
FIG. 15 is a graph of capacitance versus frequency for various dilution factors of water.
Figure 16:
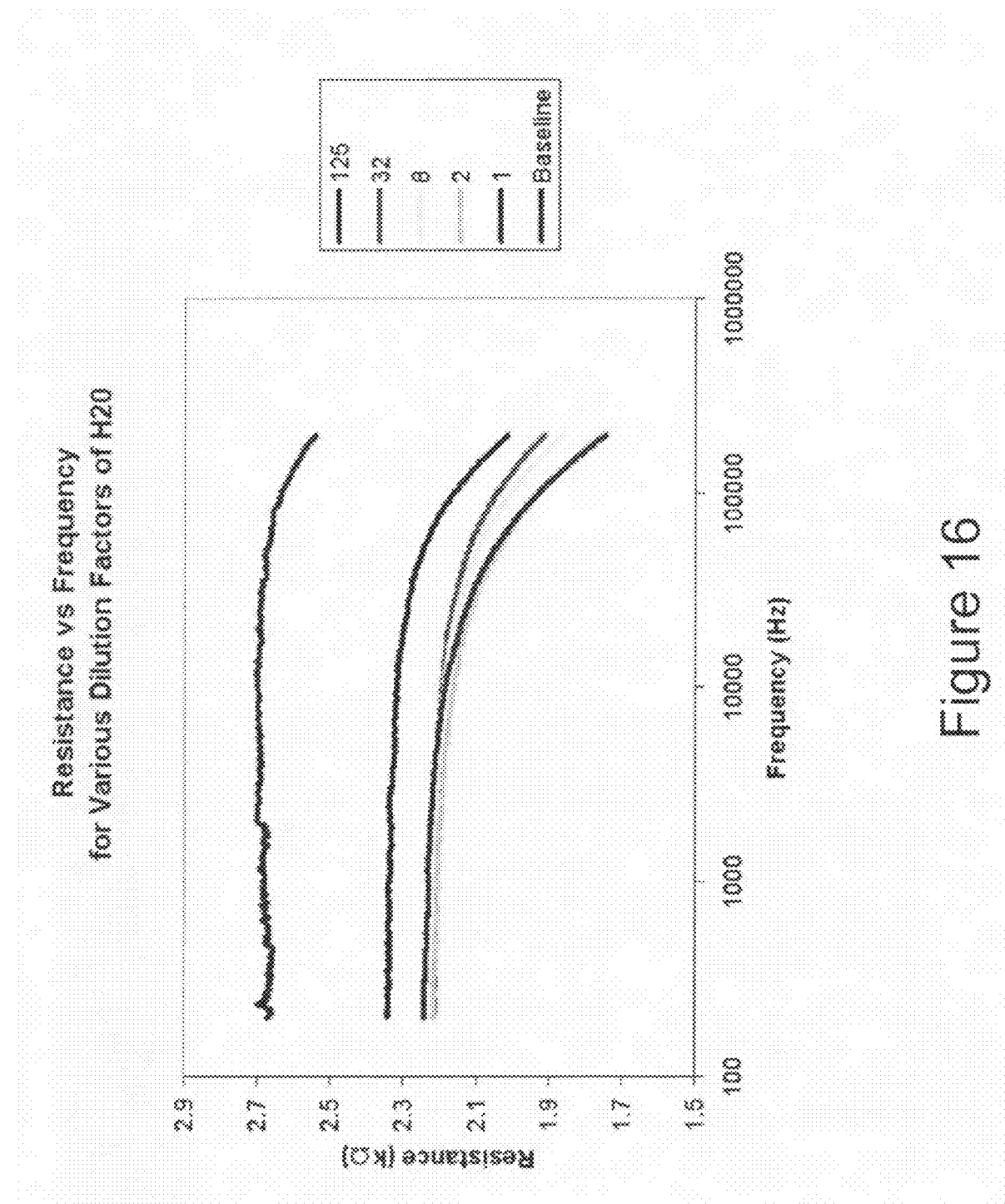
FIG. 16 is a graph of resistance versus frequency for various dilution factors of water.
Figure 17:
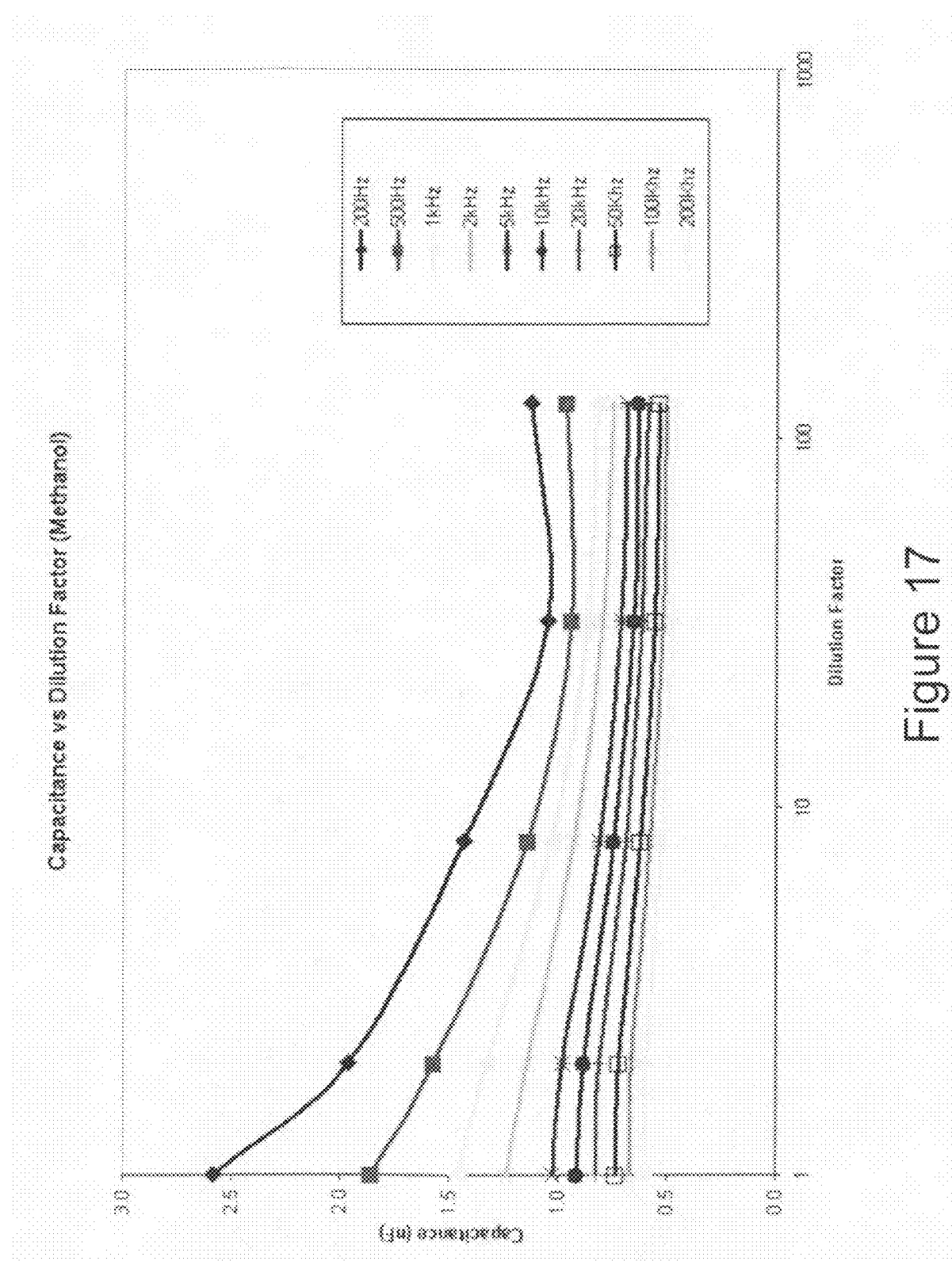
FIG. 17 is a graph of capacitance versus dilution factor for methanol.
Figure 18:
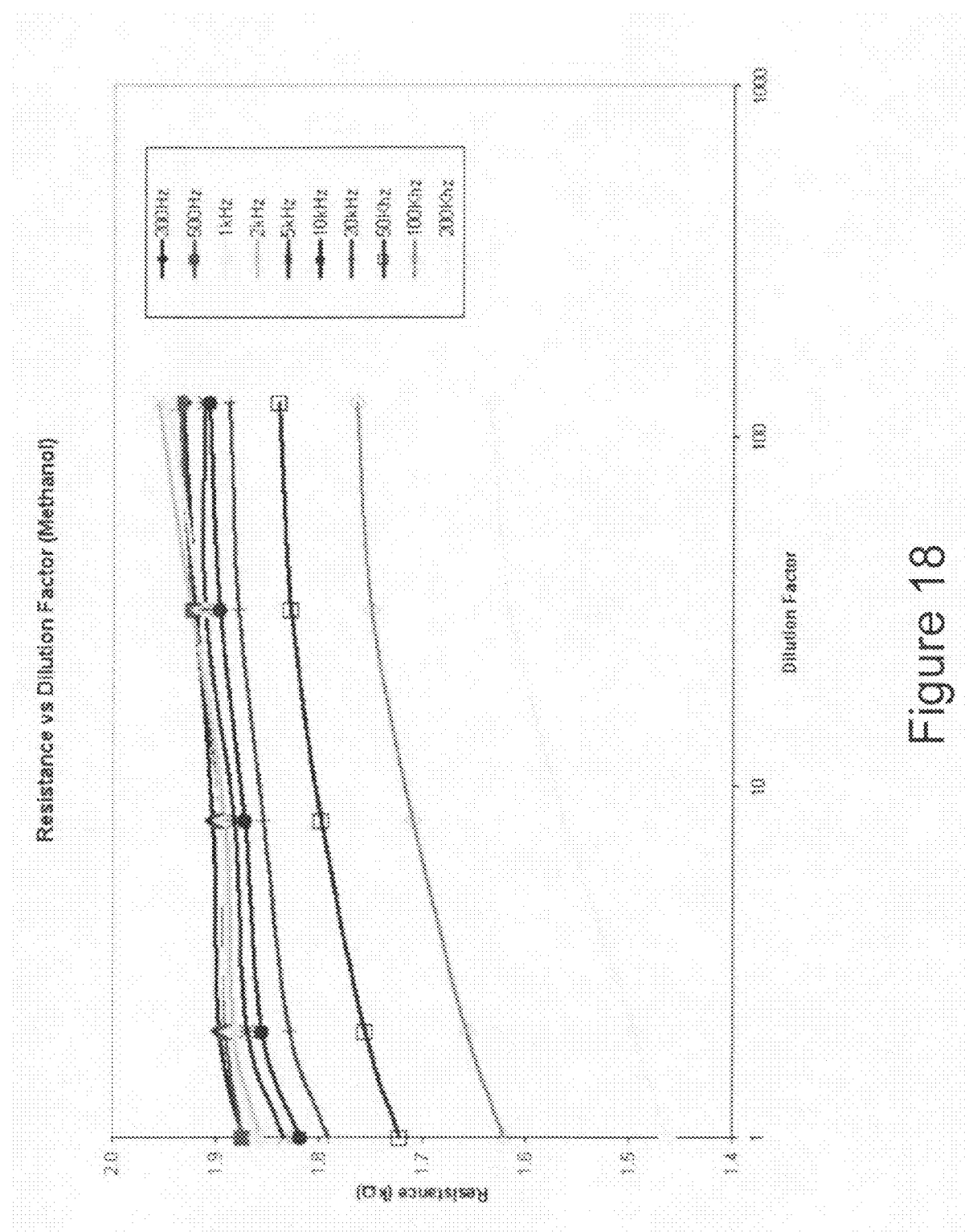
FIG. 18 is a graph of resistance versus dilution factor for methanol.
Figure 19:
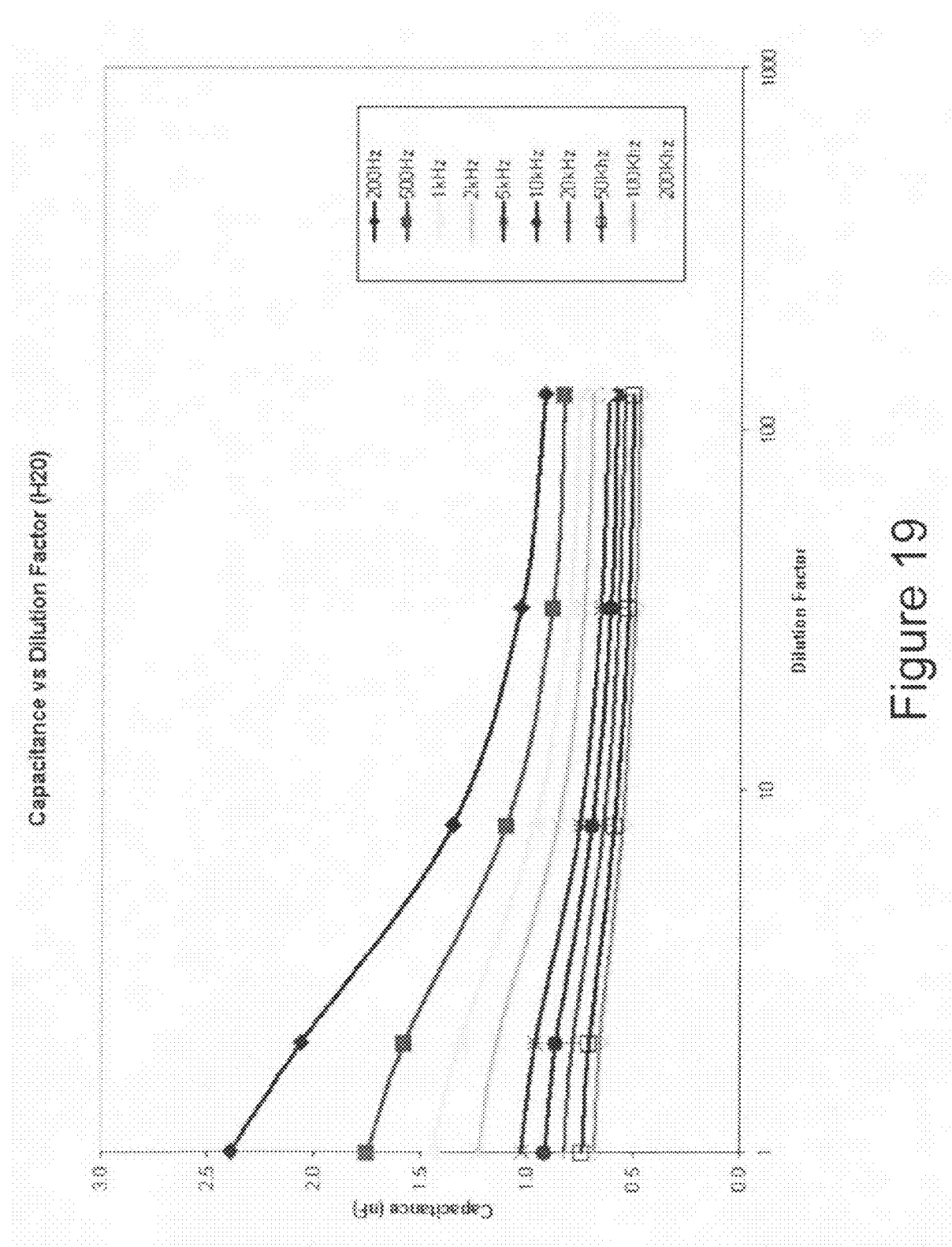
FIG. 19 is a graph of capacitance versus dilution factor for water.
Figure 20:
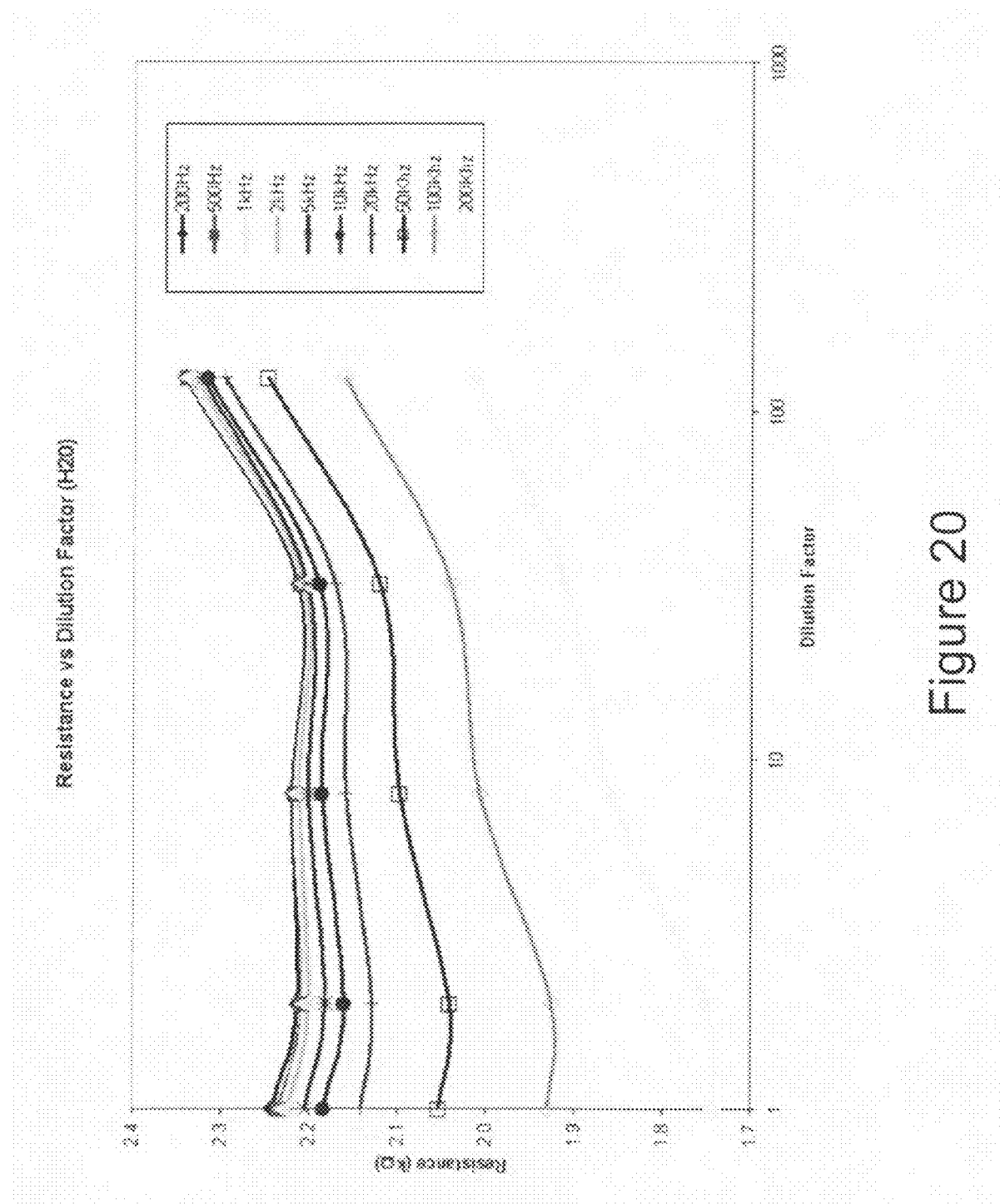
FIG. 20 is a graph of resistance versus dilution factor for water.

Organic vapors were created using a computer-controlled vapor generator. This device mixes a carrier gas (dry nitrogen) with saturated vapor, at 15 degrees C., to produce a prescribed dilution level. The impedance of the sensor, exposed to the various diluted samples, was measured using an Agilent 4980A LCR meter (Inductance-Capacitance-Resistance). The impedance model selected was the parallel resistor with a parallel capacitor. FIG. 11 and FIG. 12 show the results of measurements taken using the AAO based sensor when it was exposed to methanol and to water. The frequency range shown in this graph is 200 Hz to 200 kHz, though data was taken up to 2 MHz but didn't present any valuable data.

When the capacitance data are compared to dilution factor, the data appear to be exponential and continues to stay sequential in order. The response is in the form $$C_p = A \exp \Box B / \Box DF \Box \quad (1)$$

where Cp is the parallel capacitance, A and B are coefficients of fit. The physical significance of these coefficients has not yet been investigated.

The exponential behavior is frequency dependent and concentration dependent with the highest sensitivity happening at the lowest frequencies. FIGS. 13-16 show the behavior of the sensor at different frequencies and different dilution factors for water and methanol. The response with varying frequency is significantly different than the response of methanol at various frequencies. Resistance varied at higher concentrations of methanol, especially at higher frequencies, however when sensing water the resistance was changed from baseline but didn't change among different concentrations.

Impedance Spectroscopy

Electrical impedance spectroscopy (EIS) has been used as an analytical tool for several decades to determine the functional characteristics of surfaces with measurements performed in-situ. Conventional EIS analytical methods have typically employed a three-electrode system immersed in a buffered electrolyte and a frequency sweep is performed from DC to several kilohertz to determine the impedance characteristics of the analyte. The applications of EIS have been ubiquitous, however typical usage includes corrosion analysis and analysis of biomolecular binding to organic substrates.

The resultant EIS analysis generates a two-dimensional plot consisting of the real component (resistance) plotted along the abscissa and the imaginary component (impedance) along the ordinate. The nomenclature varies in the literature, however, these plots are commonly known as Nyquist or Cole-Cole plots [6]. In this experiment, true EIS measurements are not employed, however, the resultant complex impedance plots are generated using the capacitance and resistance data captured by an LCR meter. The observed impedance parameters varied as a function of the concentration of the analyte at the surface of the sensor.

Figure 21:
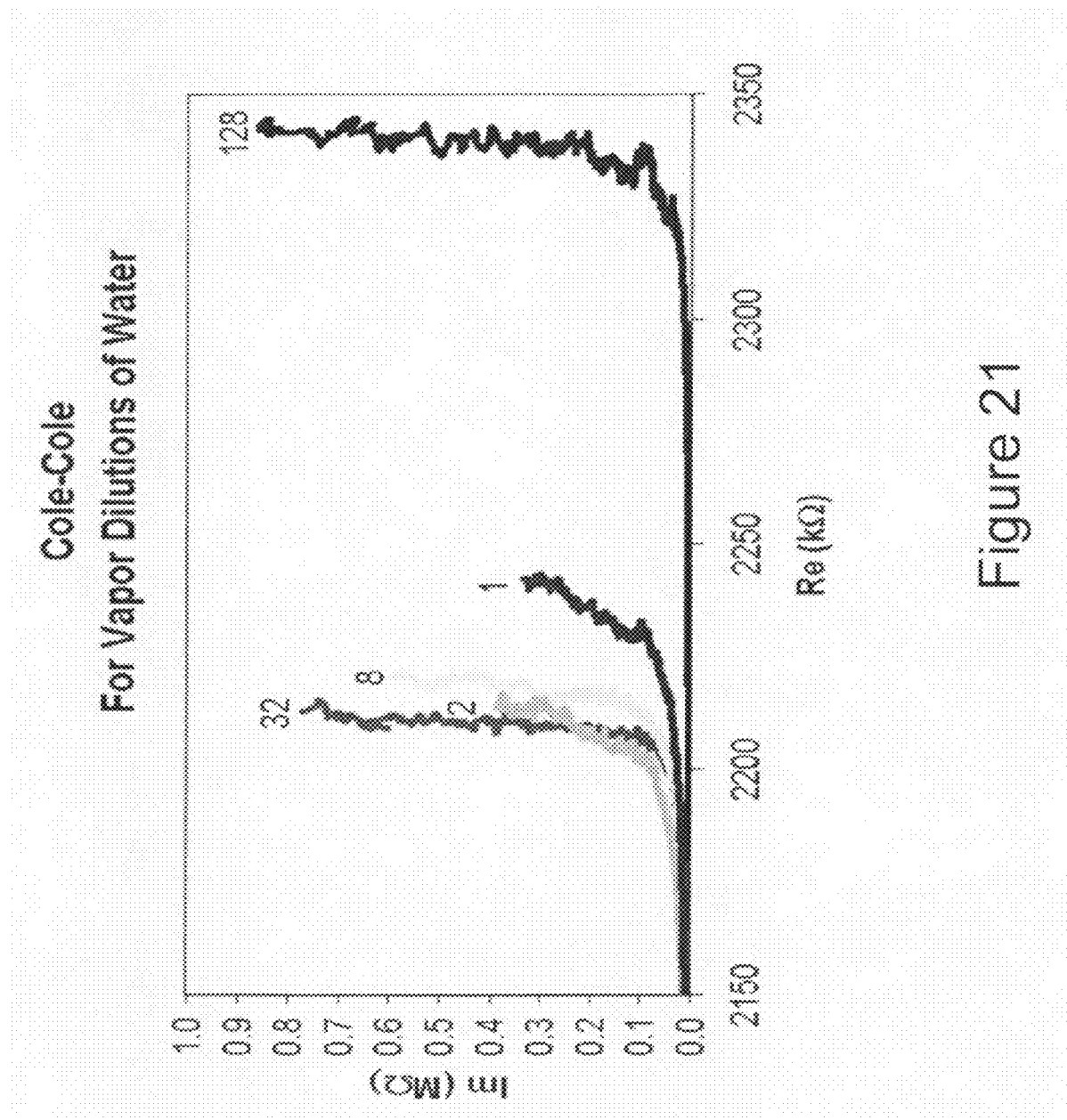
FIG. 21 is a Cole-Cole plot of vapor dilutions of water.
Figure 22:
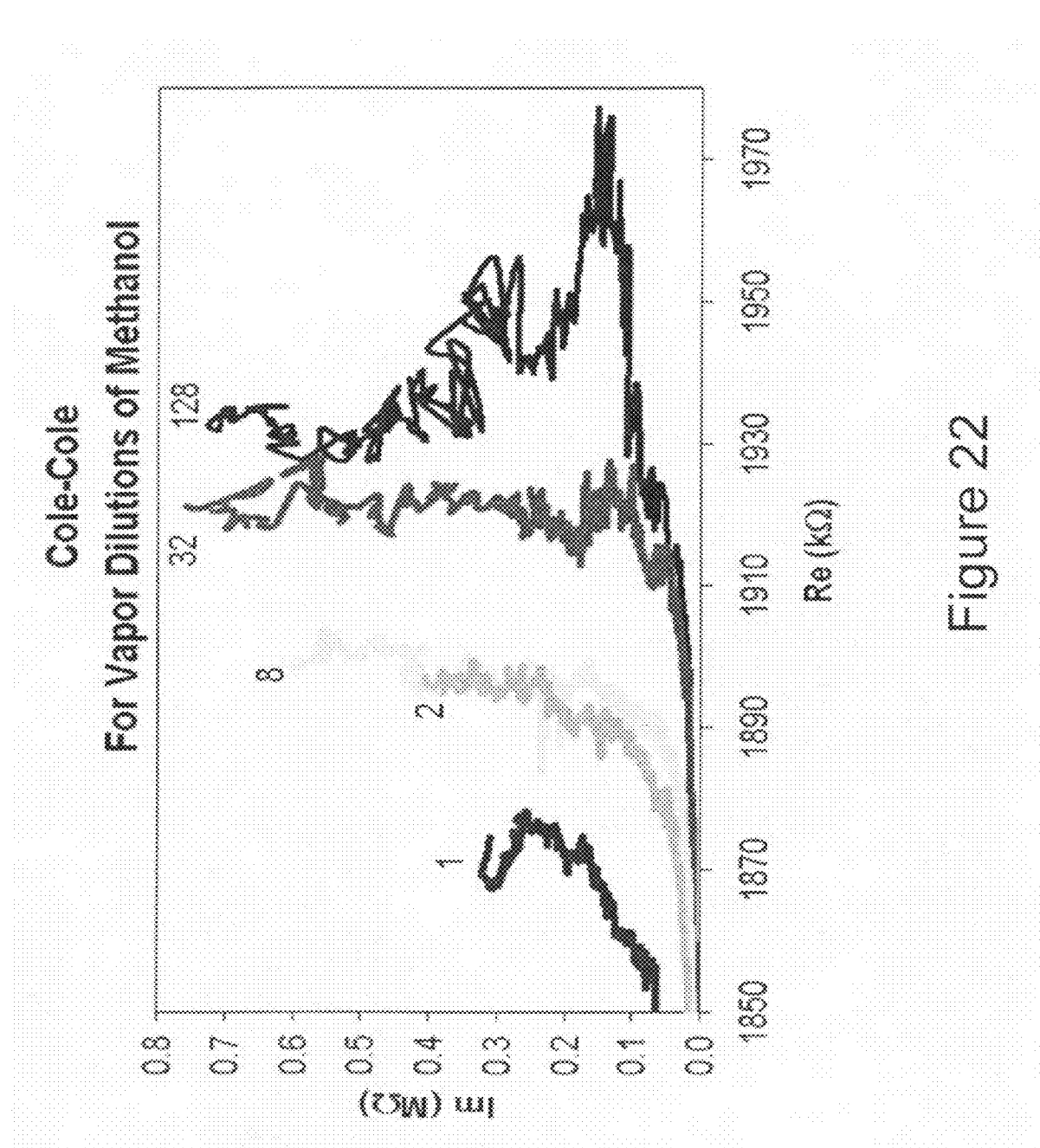
FIG. 22 is a Cole-Cole plot of vapor dilutions of methanol.

The test configuration consists of the previously mentioned Agilent HP4980A LCR meter interfaced to a host-PC for real-time frequency sweep data collection and analysis. The LCR meter front end was interfaced to the sensor's interdigitated electrodes through the use of two low impedance null probes. FIGS. 21-22 denote the parametric shift of the sensor impedance as the analyte concentration is increased. The frequency sweep corresponds to the previously shown capacitance and resistance data (FIGS. 17-20) of 200 Hz to 2 kHz with the 200 Hz initial frequency appearing at the upper right-hand data point terminating with the 2 kHz data point at the far left.

The AAO devices demonstrated in this experiment show that the nanoporous material is sensitive to organic molecules. It also can be seen from the data in FIG. 11 that methanol can be detected by using an AAO capacitive sensor. From this data set it is evident that the sensor has the ability to discriminate between water and methanol vapor. Therefore, the sensor is useful for the detection of any other molecules as well.

Figure 24:
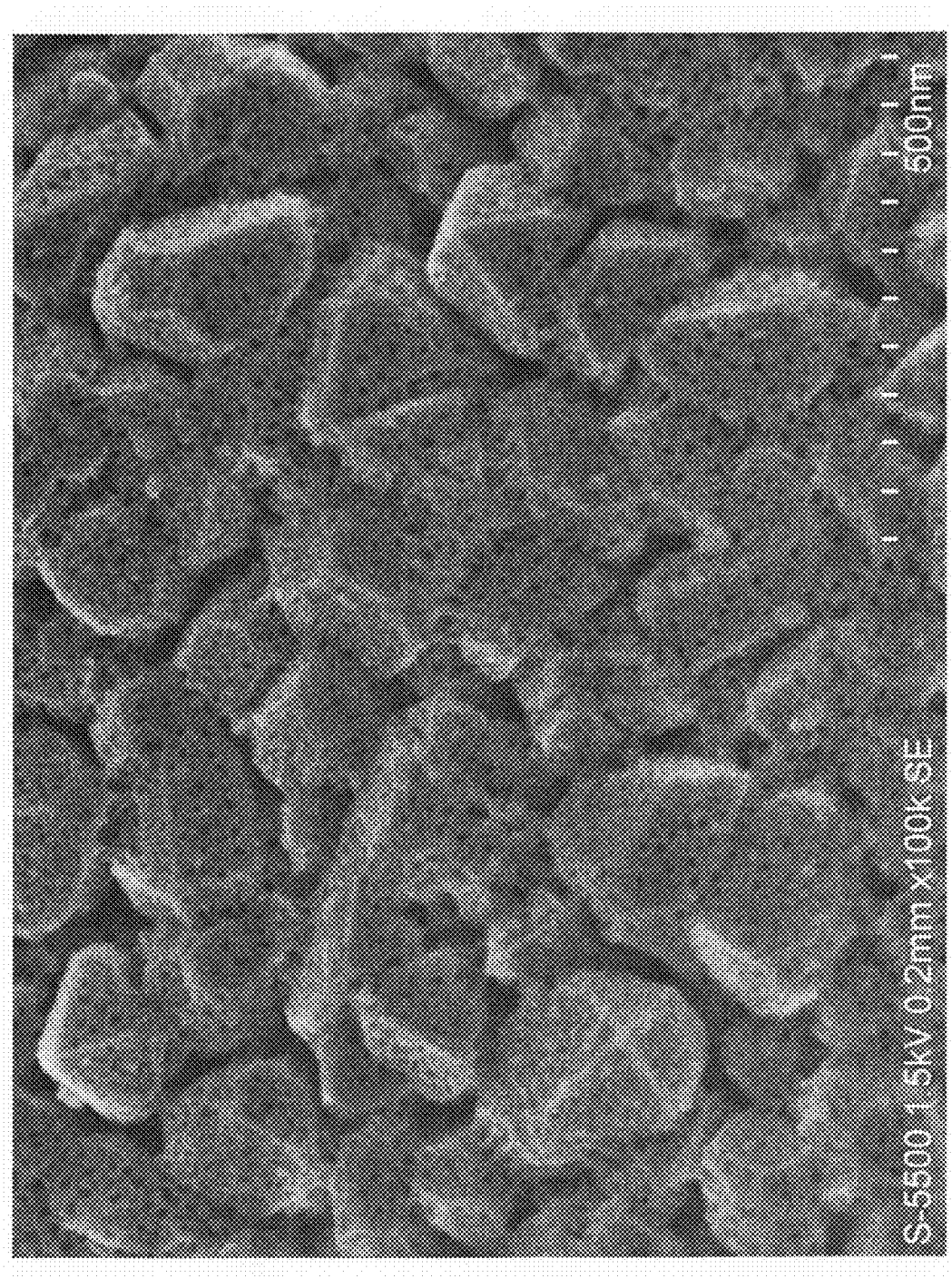
FIG. 24 is a photograph of a surface of the nano-sensor.
Figure 25:
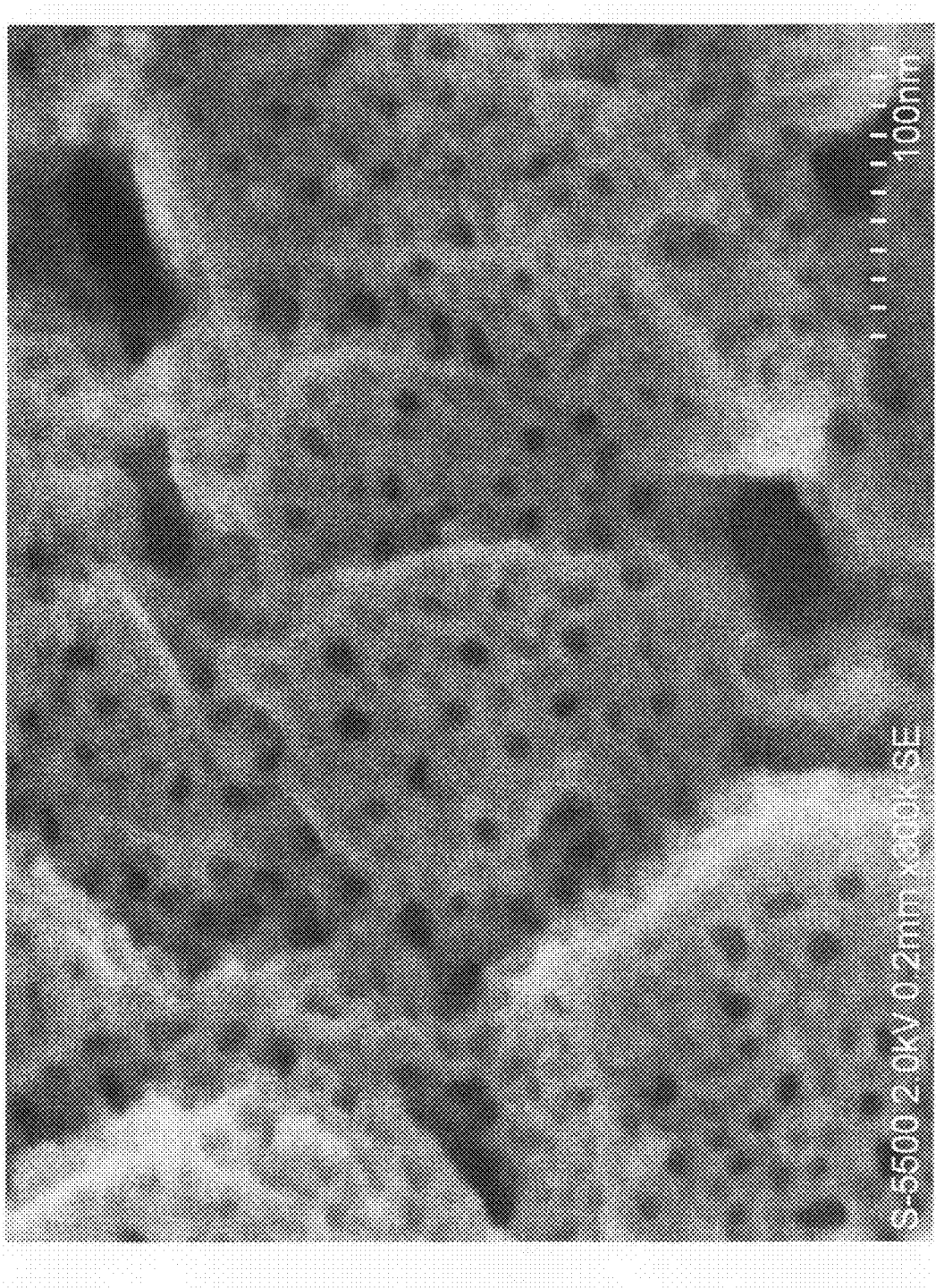
FIG. 25 is a photograph of a surface of the nano-sensor.
Figure 26:
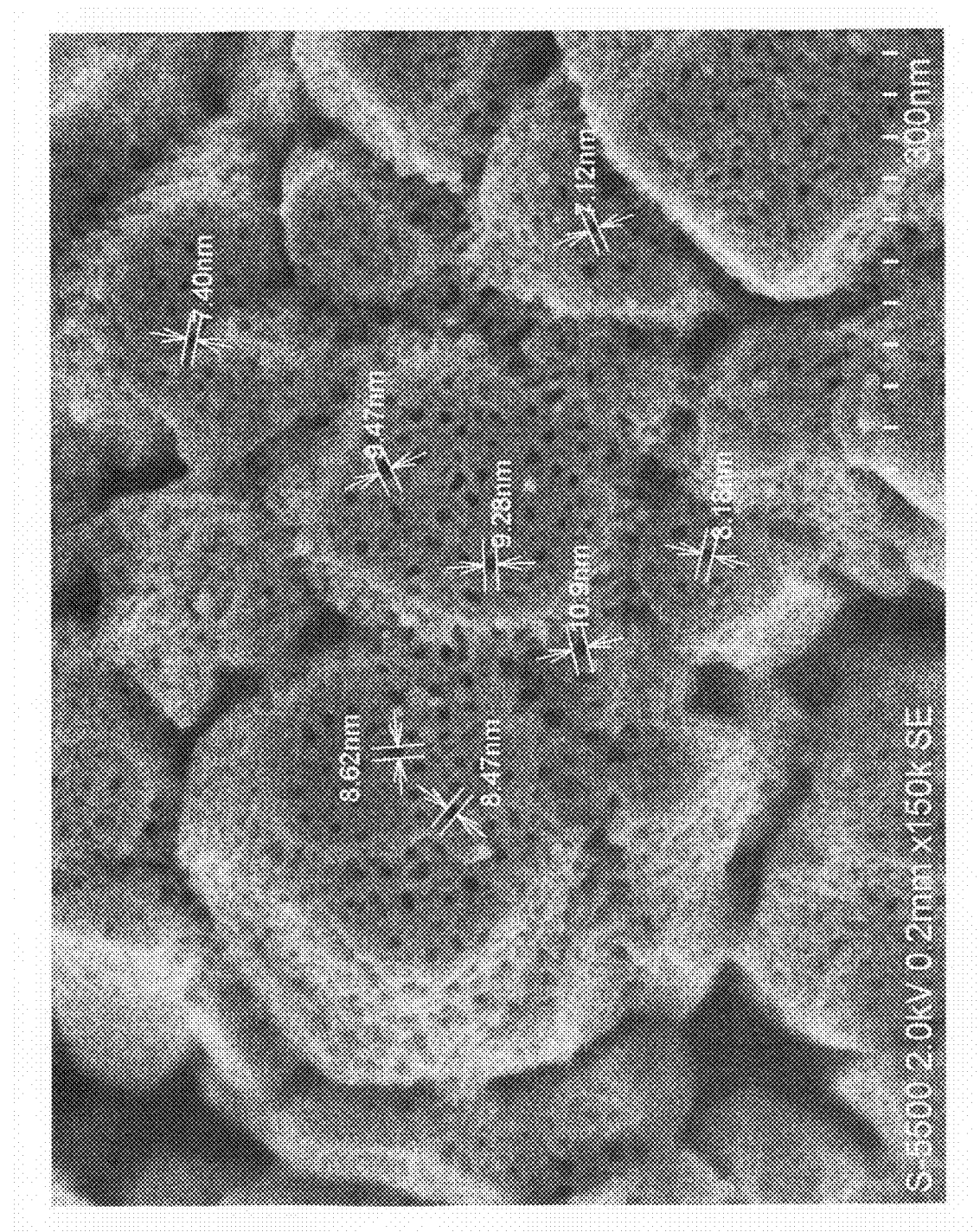
FIG. 26 is a photograph of a surface of the nano-sensor.

The morphology and composition of the substrate materials was also examined. SEM images were obtained as shown in FIGS. 24-26 of the surface of the nano-sensor 10. Secondary emission detectors enhance the signal of the imaging machine, and the system compensates for the charge build-up by scanning with a lower potential. The sensors in this analysis were anodized with less vigorous conditions. The AAO formation used 0.043 M oxalate, hence resulting in smaller pore diameters. Previously studied batches used 0.40 M oxalate, resulting in larger pores and smaller interpore distance. Also, the EDAX shows that the silica layer is very permeable to the TiW.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

1. Elizabeth C. Dickey, *, Oomman K. Varghese1, Keat G. Ong, Dawei Gong, Maggie Paulose and Craig A. Grimes, "Room Temperature Ammonia and Humidity Sensing Using Highly Ordered Nanoporous Alumina Films", *Sensors* 2002, 2, 91-110.
2. Haji-Sheikh, M. J., Andersen, M., Ervin, J. "Anodic nanoporous humidity sensing thin films for the commercial and industrial applications "Industry Applications Conference, 2004. 39th IAS Annual Meeting. Conference Record of the 2004 IEEE" Publication Date: 3-7 Oct. 2004 Volume: 2, On page(s): 1207-1210 vol. 2.
3. R. J. Lazarowich, P. Taborek, B. Y. Yoo and N. V. Myung, "Fabrication of Porous Alumina on Quartz Crystal Microbalances".
4. Oomman K. Varghese, Dawei Gong, William R. Dreschel, Keat G. Ong, Craig A. Grimes, "Ammonia detection using nanoporous alumina resistive and surface acoustic wave sensors", Sensors and Actuators B 94 (2003) 27-35.
5. Niloy Mukherjee, Maggie Paulose, Oomman K. Varghese, G. K. Mor, and Craig A. Grimes, "Fabrication of nanoporous tungsten oxide by galvanostatic anodization.", J. Mater. Res., Vol. 18, No. 10, October 2003, pp. 2296-2299.
6. Gamry Instrument Company, application note, "Basics of Electrical Impedance Spectroscopy", 31 pp.

What is claimed is:

1. A nano-sensor comprising a substrate including pores formed thereon, said substrate including an adhesion layer of titanium-tungsten and aluminum on a front side of said substrate anodized to create a nano-porous ceramic layer, detecting means for detecting changes in capacitance due to the presence of a substance, and a chemical detecting compound condensed inside said pores of acetone.

2. A nano-sensor comprising a substrate including pores formed thereon, said substrate including an adhesion layer of titanium-tungsten and aluminum on a front side of said substrate anodized to create a nano-porous ceramic layer, detecting means for detecting changes in capacitance due to the presence of a substance, and a chemical detecting compound electroplated inside said pores.

3. The nano-sensor of claim 2, wherein said chemical detecting compound is palladium.

4. The nano-sensor of claim 1, further including a hydrophobic filter operatively attached to said substrate.

5. The nano-sensor of claim 1, wherein said detecting means further includes means for separating signals from different substances.

6. A method of measuring humidity, including the steps of:
sampling air with the nano-sensor of claim 1;
detecting changes in capacitance; and
analyzing an output electrical signal that is proportional to a concentration of oxidizing or reducing agents on a surface of the nano-sensor, and determining the relative humidity of air.

7. A method of detecting the presence of a substance, including the steps of:
taking a sample with the nano-sensor of claim 1 by hydrophobically filtering molecules;
detecting changes in capacitance; and
determining the presence of a substance.

8. The method of claim 7, wherein said hydrophobically filtering step is further defined as hydrophobically filtering molecules chosen from the group consisting of isopropanol and acetone.

9. The method of claim 7, wherein said detecting changes step further includes the step of separating signals from different substances and said determining step is further defined as determining the presence of more than one substance.

10. The method of claim 7, wherein said taking a sample step is further defined as absorbing $H_2$ onto palladium inside the pores and forming palladium hydride, and said determining step is further defined as determining the presence of $H_2$.

11. The method of claim 7, wherein said detecting changes in capacitance step is further defined as detecting a disturbance in capacitance of electric current applied across the nano-sensor by a power source.

12. The method of claim 7, wherein said determining step is further defined as analyzing an output electrical signal that is proportional to a concentration of oxidizing or reducing agents on a surface of the nano-sensor, and determining the presence of a substance.

13. A method of making the nano-sensor of claim 1, including the steps of:
forming nano-pores on a substrate; and
forming, on the surface of the substrate, detecting means for detecting changes in capacitance due to the presence of a substance by polymerizing the surface of the substrate with a metal by submerging the substrate in a solution of the metal, scanning a potential to a negative direction, reducing the metal as a thin-film of the surface of the substrate, cycling the potential to a positive direction, and removing loosely bound metal.

14. The method of claim 13, further including the step of forming a hydrophobic filter on the surface of the substrate.

15. The method of claim 13, further including the step of forming a chemical detecting compound inside the pores by electroplating the chemical detecting compound inside the pores.

16. The method of claim 15, wherein said electroplating step is further defined as electroplating palladium inside the pores.

* * * * *